(12) United States Patent
Ardell et al.

(10) Patent No.: US 12,409,322 B2
(45) Date of Patent: Sep. 9, 2025

(54) TREATMENT OF CARDIAC DYSFUNCTION

(71) Applicants: The Regents of the University of California, Oakland, CA (US); Presidio Medical, Inc., South San Francisco, CA (US)

(72) Inventors: Jeffrey Laurence Ardell, Oakland, CA (US); Kalyanam Shivkumar, Oakland, CA (US); Arun Sridhar, Stevenage (GB)

(73) Assignees: The Regents of the University of California, Oakland, CA (US); Presidio Medical, Inc., San Francisco, CA (US)

( * ) Notice: Subject to any disclaimer, the term of this patent is extended or adjusted under 35 U.S.C. 154(b) by 270 days.

(21) Appl. No.: 17/808,087

(22) Filed: Jun. 21, 2022

(65) Prior Publication Data

US 2024/0042208 A1 Feb. 8, 2024

Related U.S. Application Data

(63) Continuation of application No. 16/328,090, filed as application No. PCT/EP2017/071475 on Aug. 25, 2017, now Pat. No. 11,369,793.

(60) Provisional application No. 62/379,937, filed on Aug. 26, 2016.

(51) Int. Cl.
*A61N 1/36* (2006.01)
*A61N 1/05* (2006.01)
*A61N 1/32* (2006.01)
*A61N 1/362* (2006.01)

(52) U.S. Cl.
CPC ........ *A61N 1/36114* (2013.01); *A61N 1/0556* (2013.01); *A61N 1/32* (2013.01); *A61N 1/36057* (2013.01); *A61N 1/362* (2013.01)

(58) Field of Classification Search
CPC .............. A61N 1/0556; A61N 1/36057; A61N 1/36114; A61N 1/362
See application file for complete search history.

(56) References Cited

U.S. PATENT DOCUMENTS

2005/0149146 A1\* 7/2005 Boveja ............... A61N 1/36007
607/46

\* cited by examiner

*Primary Examiner* — Scott Luan
(74) *Attorney, Agent, or Firm* — Knobbe, Martens, Olson & Bear, LLP

(57) ABSTRACT

Modulation, preferably inhibition, of neurosignaling of a cardiac-related sympathetic nerve in the extracardiac intrathoracic neural circuit is effective in stabilizing cardiac electrical and/or mechanical function, thereby providing ways of treating or preventing cardiac dysfunction such as arrhythmias.

20 Claims, 20 Drawing Sheets

TREATMENT OF CARDIAC DYSFUNCTION

TECHNICAL FIELD

This invention relates to the treatment of cardiac dysfunction. More specifically, the invention relates to medical device and systems for the treatment of cardiac dysfunction, and medical devices that deliver neuromodulatory therapy for such purposes.

BACKGROUND ART

Cardiac dysfunction refers to a pathological decline in cardiac performance. Cardiac dysfunction refers to any cardiac disorders or aberrant conditions that are associated with or induced by the various cardiomyopathies, cardiomyocyte hypertrophy, cardiac fibrosis, or other cardiac injuries. Specific examples of cardiac dysfunction include cardiac remodeling, cardiac hypertrophy, heart failure and cardiac arrhythmias Cardiac dysfunction may be manifested through one or more parameters or indicia including changes to stroke volume, ejection fraction, end diastolic fraction, stroke work, arterial elastance, or an increase in heart weight to body weight ratio.

Sudden cardiac death (SCD) is a leading cause of mortality worldwide, with approximately 300,000 people die suddenly of this cause every year in the United States. Ventricular arrhythmias are the most common reason for SCD. There are many causes of ventricular arrhythmias and SCD, including genetic predisposition, drugs and acquired causes. The majority of the patients with ventricular arrhythmias have a pre-existing pathology.

The initiation and propagation of arrhythmia has been the focus of intense research which is well documented in the literature. Cardiac injury (e.g. infarction, focal inflammation) results in the formation of a scar in the organ, leading to slowed and altered paths of electrical propagation within the myocardium. This alters the integrative regulation of the heart, creating a substrate for reentrant arrhythmias. The systemic effects of myocardium injury are characterized by activation (e.g. afferent-mediated activation) of the neuroendocrine system, primarily sympatho-excitation in conjunction with withdrawal of central parasympathetic tone, which provides short term benefits to maintain cardiac output. The recovery from acute injury is characterized by a state in which there is continued abnormal cardiac neurotransmission, such as afferent signaling (cardio-centric afferents). Mechanistically, such dysregulation reflects reactive and adaptive responses of the cardiac neural hierarchy leading to changes in sensory transduction of the diseased myocardium and resulting in altered neuronal network excitability. Such changes in neural processing are manifest in intrathoracic neural circuit, spinal cord, brainstem and higher centers of the CNS. The reorganization ultimately leads to conflict between central and peripheral aspects of the hierarchy. This altered neural processing leads to maladaptive responses ultimately resulting in excessive sympatho-excitation and reduced parasympathetic drive. These neural adaptations contribute to the evolution of pump failure and fatal arrhythmias.

Cardiac arrhythmias are routinely treated with medication, ablative and device therapy, e.g. implantable cardioverter defibrillator (ICD). Despite the current standard of care, there are many patients who are either refractory to anti-arrhythmic medications, or new focal ablations created during catheterization procedures only offer temporary relief as they themselves can become blocks for electrical wave propagation, therefore ventricular arrhythmias recur. ICDs have been associated with a poor prognosis [1,2].

The direct evidence showing impact of sympathetic signaling leading to cardiac arrhythmia came from a patient case study in whom antiarrhythmic and ICD therapy failed and the patient continued to suffer from high incidence of ICD shocks and skin burns as a result. This patient was treated in the emergency room and the final controlling mechanism for arrhythmia management was initiation of thoracic epidural anesthesia (TEA). TEA resulted in complete cessation of shocks for up to 48 hours. This was further explored in patients with incessant ventricular tachycardia (VT) in whom the sympathetic paravertebral ganglia (T1-T4) were excised which led to reduction in the frequency of ICD shocks, suggesting that neural control of cardiac excitability may be exploited for arrhythmia treatment.

Attempts to treat ventricular arrhythmias include targeting elements within the cardiac sympathetic nervous system by electrical stimulation or transection. It was found that such an approach applied to the paravertebral chain can modulate autonomic imbalances and reduce arrhythmias.

One surgical approach involves the resection (unilateral or bilateral) of stellate ganglion. Left and bilateral cardiac sympathetic denervation have been shown to impart anti-arrhythmic effects in patients with refractory ventricular arrhythmias or electrical storm [3]. Left cardiac sympathetic denervation (LCSD) has been shown to be effective in preventing life-threatening ventricular arrhythmias [4,5,6]. It was found that LCSD raised the threshold for ventricular fibrillation (VF), which means that, independently of the underlying condition, VF is less likely to initiate. Historically, these surgical procedures remove all connections from spinal cord neurons to adrenergic and other neuronal somata in the thorax. Recently, these surgical approaches have been modified to surgically remove the caudal two-thirds of the stellate ganglion along with their respective paravertebral chains down to the T4 paravertebral ganglia. Although such surgical approaches have documented anti-arrhythmic effects, lack of clear delineation and visualization of cardiac specific neurons at the time of stellate decentralization leads to adverse effects like Horner syndrome and anhydrosis [7], hyperalgesia [8]. Furthermore, these effects are irreversible.

There remains an urgent need for further and improved treatments of cardiac dysfunction, in particular, those that confer minimal impact on basal cardiac function.

SUMMARY OF THE INVENTION

The inventors found that reversible modulation (e.g. inhibition) of the neural activity of cardiac-related sympathetic nerves in the extracardiac intrathoracic neural circuit significantly decreases arrhythmia risk in animal models. Thus, reversible and scalable inhibition of the neural activity of a cardiac-related sympathetic nerve in the extracardiac intrathoracic neural circuit is capable of treating or preventing cardiac dysfunction.

More specifically, the inventors identified that inhibiting the sympathetic projections at a *nexus* intervention point in the extracardiac intrathoracic neural circuit (e.g. at the ansae subclavia or at the T1-T2 paravertebral ganglia) is effective in stabilizing cardiac electrical and/or mechanical function. The nerve conduction in the sympathetic chain ganglia (or in the case of ansae subclavian within axons of passage) can be reversibly inhibited using electrical signals to create a finite region of axons through which action potentials cannot pass. This neural modulation is scalable and includes afferent and efferent nerve projections. This overrides integrated central control of sympathetic activity, decreasing ventricular excitability leading to a reduction in arrhythmia risk. One particular advantage is that there is minimal effect on the basal cardiac function, but with efficacy on evoked neural responses. Furthermore, upon cessation of electrical signals, the inhibition ceases and multi-level cardiac reflex control resumes. These advantages are demonstrated in the examples below.

Thus, the invention provides a method of treating or preventing cardiac dysfunction in a subject by reversibly inhibiting neural activity of a cardiac-related sympathetic nerve in the extracardiac intrathoracic neural circuit. For example, the invention provides a method of treating ventricular arrhythmias post-myocardial infarction. A preferred way of reversibly inhibiting the cardiac-related sympathetic nerve activity uses a device or system which applies a signal to the cardiac-related sympathetic nerve in the extracardiac intrathoracic neural circuit.

The invention also provides a method of treating or preventing cardiac dysfunction in a subject, comprising applying a signal to a cardiac-related sympathetic nerve in the extracardiac intrathoracic neural circuit in the subject to reversibly inhibit the neural activity of the cardiac-related sympathetic nerve. In some embodiments, the method is for treating ventricular arrhythmias post-myocardial infarction.

The invention provides an implantable device or system according to the invention comprising at least one transducer, preferably an electrode, suitable for placement on or around a cardiac-related sympathetic nerve in the extracardiac intrathoracic neural circuit, and a signal generator for generating a signal to be applied to the cardiac-related sympathetic nerve via the at least one transducer such that the signal reversibly inhibits the neural activity of the cardiac-related sympathetic nerve to produce a physiological response in the subject. The physiological response may be a decrease in a chronotropic, a dromotropic, a lusitropic and/or an inotropic evoked response. In some embodiments, the cardiac-related sympathetic nerve is an efferent nerve. In some embodiments, the signal is KHFAC, CBDCC, or a hybrid thereof.

The invention also provides a method of treating or preventing cardiac dysfunction in a subject, comprising: (i) implanting in the subject a device or system of the invention; (ii) positioning the transducer of the device or system in signaling contact with a cardiac-related sympathetic nerve in the extracardiac intrathoracic neural circuit in the subject; and optionally (iii) activating the device or system. In some embodiments, the method is for treating ventricular arrhythmias post-myocardial infarction.

Similarly, the invention provides a method of reversibly inhibiting neural activity in a subject's cardiac-related sympathetic nerve in the extracardiac intrathoracic neural circuit, comprising: (i) implanting in the subject a device or system of the invention; positioning the transducer in signaling contact with the subject's cardiac-related sympathetic nerve; and optionally (iii) activating the device or system.

The invention also provides a method of implanting a device or a system of the invention in a subject, comprising: positioning a transducer of the device or system in signaling contact with the subject's cardiac-related sympathetic nerve in the extracardiac intrathoracic neural circuit.

The invention also provides a device or a system of the invention, wherein the device or system is attached to a cardiac-related sympathetic nerve in the extracardiac intrathoracic neural circuit.

The invention further provides a neuromodulatory (e.g. neuroinhibitory) electrical waveform for use in treating or preventing cardiac dysfunction in a subject, wherein the waveform is comprised of a plurality of repeating cycles of DC pulses, each cycle comprising a plurality of DC pulses applied sequentially at different locations on the subject's cardiac-related sympathetic nerve in the extracardiac intrathoracic neural circuit such that when applied to a subject's cardiac-related sympathetic nerve in the extracardiac intrathoracic neural circuit, the waveform reversibly inhibits neural activity in the cardiac-related sympathetic nerve in the extracardiac intrathoracic neural circuit. In some embodiments, the neuromodulatory electrical waveform is for use in treating ventricular arrhythmias post-myocardial infarction.

The invention further provides a plurality of neuromodulatory (e.g. neuroinhibitory) electrical waveforms for use in treating or preventing cardiac dysfunction in a subject, wherein each waveform is comprised of a plurality of charge-balanced DC pulses, the plurality of waveforms applied sequentially at a corresponding plurality of locations on the subject's cardiac-related sympathetic nerve in the extracardiac intrathoracic neural circuit such that when applied to a subject's cardiac-related sympathetic nerve in the extracardiac intrathoracic neural circuit, the plurality of waveforms reversibly inhibit neural activity in the cardiac-related sympathetic nerve in the extracardiac intrathoracic neural circuit. In some embodiments, the plurality of neuromodulatory electrical waveforms are for use in treating ventricular arrhythmias post-myocardial infarction.

Before effecting modulation (e.g. becoming inhibitory), electrical signaling can be preceded by a short period in which the nerve is instead stimulated (an "onset response" or "onset effect"). Various ways of avoiding an onset response are available. In certain embodiments, an onset response as a result of the signal being applied can be avoided if the signal does not have a frequency of 20 kHz or lower, for example 1-20 kHz, or 1-10 kHz. Frequency- and amplitude-transitioned waveforms to mitigate onset responses in high-frequency nerve blocking are described by Gerges et al. [9]. Amplitude ramping can also be used, as discussed by Bhadra et al. [10], or a combination of KHFAC with charge balanced direct current waveforms can be used [11]. A combination of KHFAC and infra-red laser light ('ACIR') has also been used to avoid onset responses [12].

In certain embodiments, the waveform comprises a DC ramp and a KHFAC waveform that commences during the DC ramp. In particular embodiments, the waveform comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially.

In certain embodiments, the waveform comprises a kilohertz frequency alternating current (KHFAC) waveform, a charge-balanced direct current carousel (CBDCC) waveform, or a hybrid thereof.

Of course, associated devices configured to apply such signals, and method of applying such signals are also possible, as described elsewhere herein.

The invention also provides the use of a neuromodulatory (e.g. neuroinhibitory) device or system for treating or preventing cardiac dysfunction in a subject, by reversibly inhibiting neural activity in the subject's cardiac-related sympathetic nerve in the extracardiac intrathoracic neural circuit. In some embodiments, the use is for treating ventricular arrhythmias post-myocardial infarction.

The invention also provides a charged particle for use in a method of treating or preventing cardiac dysfunction, wherein the charged particle causes reversible depolarization or hyperpolarization of the nerve membrane, such that an action potential does not propagate through the modified nerve. In some embodiments, the use is in a method of treating ventricular arrhythmias post-myocardial infarction.

The invention also provides an electrical waveform for use in a method of treating or preventing cardiac dysfunction, wherein a charged particle elicited by the electrical waveform causes reversible depolarization or hyperpolarization of the nerve membrane, such that an action potential does not propagate through the modified nerve. In some embodiments, the plurality of electrical waveforms are for use in treating ventricular arrhythmias post-myocardial infarction.

The invention also provides a modified cardiac-related sympathetic nerve m the extracardiac intrathoracic neural circuit to which a transducer of the system or device of the invention is attached. The transducer is in signaling contact with the nerve and so the nerve can be distinguished from the nerve in its natural state. Furthermore, the nerve is located in a patient who suffers from, or is at risk of, cardiac arrhythmia.

The invention also provides a modified cardiac-related sympathetic nerve in the extracardiac intrathoracic neural circuit, wherein the neural activity is reversibly inhibited by applying a signal to the cardiac-related sympathetic nerve in the extracardiac intrathoracic neural circuit. In some embodiments, the signal is KHFAC, CBDCC, or a hybrid thereof.

The invention also provides a modified cardiac-related sympathetic nerve in the extracardiac intrathoracic neural circuit, wherein the nerve membrane is reversibly deploarized or hyperpolarized by an electric field, such that an action potential does not propagate through the modified nerve. In some embodiments, the electrical field is caused by applying a signal to the nerve, where the signal is optionally KHFAC, a CBDCC, or a hybrid thereof.

The invention also provides a modified cardiac-related sympathetic nerve in the extracardiac intrathoracic neural circuit bounded by a nerve membrane, comprising a distribution of potassium and sodium ions movable across the nerve membrane to alter the electrical membrane potential of the nerve so as to propagate an action potential along the nerve in a normal state; wherein at least a portion of the nerve is subject to the application of a temporary external electrical field which modifies the concentration of potassium and sodium ions within the nerve, causing depolarization or hyperpolarization of the nerve membrane, thereby temporarily blocking the propagation of the action potential across that portion in a disrupted state, wherein the nerve returns to its normal state once the external electrical field is removed. In some embodiments, the electrical field is caused by applying a signal to the nerve, where the signal is optionally KHFAC, a CBDCC, or a hybrid thereof.

The invention also provides a modified cardiac-related sympathetic nerve in the extracardiac intrathoracic neural circuit obtainable by reversibly inhibiting neural activity of the cardiac-related sympathetic nerve according to a method of the invention.

The invention also provides a method of modifying the cardiac-related sympathetic nerve in the extracardiac intrathoracic neural circuit's activity, comprising a step of applying a signal to the cardiac-related sympathetic nerve in the extracardiac intrathoracic neural circuit in order to reversibly inhibit the neural activity of the cardiac sympathetic nerve in a subject. Preferably the method does not involve a method for treatment of the human or animal body by surgery. The subject already carries a device or system of the invention which is in signaling contact with a cardiac-related sympathetic nerve in the extracardiac intrathoracic neural circuit.

The invention also provides a method of controlling a device or system of the invention which is in signaling contact with a cardiac-related sympathetic nerve in the extracardiac intrathoracic neural circuit, comprising a step of sending, preferably externally sending, control instructions to the device or system, in response to which the device or system applies a signal to the cardiac-related sympathetic nerve in the extracardiac intrathoracic neural circuit.

DETAILED DESCRIPTION OF THE INVENTION

Cardiac-related sympathetic nerve in the extracardiac intrathoracic neural circuits The invention involves modulation (e.g. inhibition) of the neural activity of a cardiac-related sympathetic nerve in the extracardiac intrathoracic neural circuit. By modulating the sympathetic neural signals to the heart, it is possible to achieve therapeutic effects. For example, inhibiting the sympathetic neural signals to the heart may decrease the chronotropic, dromotropic, lusitropic and/or inotropic evoked responses of the heart, leading to stabilization of the cardiac electrical and/or mechanical function (e.g. restoring heart rate, heart rhythm, contractility and blood pressure towards normal baseline levels), thereby decreasing the risk of cardiac dysfunction.

The autonomic nervous system exerts a strong influence on cardiac function [13]. The major sources of cardiac innervations are from the brainstem/vagus and the spinal cord/intrathoracic sympathetic ganglia. These extracardiac parasympathetic and sympathetic nerves carry afferent and efferent information, and communicate and control cardiac function via several ganglia on the heart. Within these intra-cardiac ganglia, there are many intra-cardiac neurons that intercommunicate and process information, such as incoming efferent information, and preferably act to both filter and augment the afferent signals, forming a tight hierarchy of neural circuits. The neural circuits also form interacting feedback loops to provide physiological stability for maintaining normal rhythm and life-sustaining circulation. These nested feedback loops ensure that there is fine-tuned regulation of efferent (sympathetic and parasympathetic cardiomotor) neural signals to the heart in normal and stressed hearts. These neural elements comprise the intrinsic cardiac nervous system which interact with extracardiac ganglia and the central elements of the nervous system to dynamically control heart function.

Cardiac-related sympathetic efferent preganglionic neurons originate in the intermediolateral column of the spinal cord and project their axons via the C7-T6 rami into the paravertebral chain (e.g. [7, 14, 15, 16, 17, 18]). From there, the cardiac-related preganglionic fibers project to sympathetic efferent postganglionic neuronal somata contained in the superior cervical, middle cervical, mediastinal ganglia and stellate ganglia. The primary interconnection between the stellate, middle cervical and the mediastinal ganglia is via the dorsal and ventral ansae subclavia [19]. FIG. 1 provides a schematic diagram of the gross anatomic arrangement of these nerves.

The invention modulates (e.g. inhibits) the neural activity of a cardiac-related sympathetic nerve in the extracardiac intrathoracic neural circuit. This modulation (e.g. inhibition) may involve efferent, afferent, or both afferent and efferent, neurons. This modulation (e.g. inhibition) may involve fibers of passage or synaptic processing with intrathoracic ganglia.

Within the extracardiac intrathoracic neural circuit, the cardiac-related sympathetic nerve may be modulated (e.g. inhibited) at the sympathetic paravertebral chain, e.g. between the lower cervical (e.g. inferior cervical ganglia) and upper thoracic paravertebral chain (e.g. T1-T4 ganglia). A cardiac-related sympathetic nerve may be modulated (e.g. inhibited) at or caudal to the middle cervical ganglion. Elements along and arising from the paravertebral chain that are caudal to the middle cervical ganglion include the ansae subclavia and the inferior cervical ganglion.

The inferior cervical ganglion is fused with the first thoracic ganglion (T1) to form a single structure called the stellate ganglion in around 80% of the human population. Thus, the cardiac-related sympathetic nerve may be modulated (e.g. inhibited) at or caudal to the inferior cervical ganglion or the stellate ganglion in the paravertebral chain.

The ansae subclavia are nerve cords that surround the subclavian artery, and form the primary interconnection between the stellate, middle cervical and the mediastinal ganglia [19]. The dorsal ansae subclavia arise as a craniomedial extension of the stellate ganglion and are usually shorter and thicker than the ventral ansae, which loop anteriorly around the subclavian artery. There is anatomical heterogeneity in that each individual may have one or more ansae subclavia. For example, the ansae subclavia can exist as single or multiple nerve cords, and the right side tends to have more nerve cords in total than the left. There are variations according to the origin and termination of the loop, for example, in some individuals no distinct dorsal ansae can be seen because the stellate and the inferior—most middle cervical ganglia form a large swelling. The invention may be applied to one or more of the ansae subclavia.

The invention preferably modulates (e.g. inhibits) at or caudal to the ansae subclavia. This is because the ansae subclavia represents the lowest *nexus* point in the cardiac nervous system hierarchy for sympathetic projection to the heart that is amenable to transducer attachment. From the ansae subclavia, the cardiac-related sympathetic nerves become more diffused so it is practically more difficult to target them. Inhibiting neural activity at the ansae subclavia is particularly effective in affecting cardiac electrical and/or mechanical function, including rhythm and contractility, as demonstrated in the examples below. The site of modulation (e.g. inhibition) may be at the junction between the dorsal and ventral rami of the ansae subclavia adjacent to the stellate ganglion.

Since the invention involves reversibly inhibiting a cardiac-related sympathetic nerve, the risks of complications associated with stellate ganglion block [20], e.g. Homer's syndrome, intra-arterial or intravenous injection, difficulty swallowing, vocal cord paralysis, epidural spread of local anaesthetic and pneumothorax, will be minimized. Blocking at the inferior cervical ganglion is undesirable because it can inhibit pain detection.

A cardiac-related sympathetic nerve may be modulated (e.g. inhibited) at or cranial to the T4 ganglion along the paravertebral chain. Preferably, the inhibition is at or cranial to the T3 ganglion along the paravertebral chain, which includes the ansae subclavia. The inhibition may be at or cranial to the T2 ganglion along the paravertebral chain. Preserving the T3 element and the more caudal elements of the paravertebral chain is useful because they are associated with sensory and sympathetic motor control of upper limb, neck and thoracic wall, so the risks for upper limb and thoracic wall pain syndromes and anhydrosis can be minimized. The invention therefore preferably inhibits neural activity of a cardiac-related sympathetic nerve at a site along the paravertebral chain that is cranial to the T3 ganglion. The invention preferably does not inhibit the neural activity of a cardiac-related sympathetic nerve at the T3 ganglion.

The invention may modulate (e.g. inhibit) a cardiac-related sympathetic nerve at any site along the paravertebral chain (which includes the ansae subclavia) between the middle cervical and T4 ganglia, between the middle cervical and T3 ganglia, or between the middle cervical and T2 ganglia. The inhibition may be at any site along the paravertebral chain between the inferior cervical and T4 ganglia, between the inferior cervical and T3 ganglia, or between the inferior cervical and T2 ganglia. The inhibition may be at any site along the paravertebral chain between the ansae subclavia and T4 ganglion, between the ansae subclavia and T3 ganglion, or between the ansae subclavia and T2 ganglion. The inhibition may be at any site along the paravertebral chain between the stellate and T4 ganglia, between the stellate and T3 ganglia, or between the stellate and T2 ganglia. The inhibition may be at any site along the paravertebral chain between the T1 and T4 ganglia, between the T1 and T3 ganglia, or between the T1 and T2 ganglia.

Preferably, the cardiac-related sympathetic nerve is inhibited at a site along the paravertebral chain between the stellate ganglion and the T4 ganglion.

The invention preferably modulates (e.g. inhibits) neural activity of a cardiac-related sympathetic nerve between the T2 ganglion and the ganglion cranial to T2, which may be the stellate ganglion or the T1 ganglion. The specific anatomical structure that is inhibited would depend on the anatomical arrangement of the individual. This region has been shown to be particularly effective for inhibiting neural activity, as demonstrated in the examples below. This region is amenable for electrodes attachment. Also, inhibition of neural activity in this region minimizes adverse or off-target effects, as explained above.

Ideally, the cardiac-related sympathetic nerve to be inhibited is amenable to transducer (e.g. electrode) attachment. For example, the nerve is accessible for an electrode attachment, and is not obstructed by ganglia, branching nerves, other nerves or blood vessels. For example, Study 4 shows that the region at the paravertebral ganglion between the T1 and T2 levels is amenable to electrode attachment, e.g. DC carousel (DCC) electrodes. As well as being accessible, the T1-T4 region tends to be consistent from patient to patient, thus facilitating this site for general use. The T1-T4 and T1-T2 regions have been previously used as a point of intervention [21].

Plasticity exists for cardiac-related sympathetic nerves in the extracardiac intrathoracic neural circuits. For example, neural remodeling including neuron cell body hypertrophy, increased fibrosis, and increased synaptic density have been shown to occur in the left and in both stellate ganglia in patients with cardiomyopathy and in an animal model of myocardial infarction [22,23]. Thus, the exact site for inhibiting neural activity may vary from human to human, but is nonetheless within the extracardiac intrathoracic neural circuit as explained above.

Typically, the invention involves modulation (e.g. inhibition) of a cardiac-related sympathetic nerve in the extracardiac intrathoracic neural circuit that is located in a bundle of nerves, e.g. in the sympathetic paravertebral chain or in the ansae subclavia. The invention may therefore involve inhibition of one or more cardiac-related sympathetic nerves.

The sympathetic paravertebral chain lies on either side of the vertebral column and essentially extends along its length. Thus, when the invention refers to a cardiac-related sympathetic nerve in the sympathetic paravertebral chain and/or its elements (e.g. ansae subclavia), it may be referring to the right and/or left sympathetic paravertebral chain and/or its elements (e.g. ansae subclavia). Hence, the invention may refer to modulation (e.g. inhibition) of cardiac-related sympathetic nerve bilaterally at the sympathetic paravertebral chain and/or its elements (e.g. ansae subclavia). The invention may refer to inhibition of a cardiac-related sympathetic nerve unilaterally at the sympathetic paravertebral chain and/or its elements (e.g. ansae subclavia).

Inhibition of neural activity of one instead of both sides is sufficient for achieving beneficial physiological effects. This is useful for the invention because it minimizes the interruption of neural activity, thereby minimizes any adverse off-target effects. The examples below shows that neural block of the right T1-T2 paravertebral chain are effective in stabilizing cardiac electrical and/or mechanical function. This is consistent with previous animal studies showing that sectioning either the right or the left ansae subclavia abolished all cardiac effects produced by stimulating that ganglion [24]. Thus, the invention inhibits a cardiac-related sympathetic nerve at either the right or the left sympathetic paravertebral chain and/or its elements (e.g. ansae subclavia). For example, the invention may inhibit a cardiac-related sympathetic nerve at the right and/or the left ansae subclavia. The invention may inhibit a cardiac-related sympathetic nerve at the right and/or the left T1-T2 paravertebral chain.

For example, the invention may involve modulation (e.g. inhibition) of a cardiac-related sympathetic nerve at one or more sites selected from the group consisting of: mediastinal ganglion, right middle cervical ganglion, left middle cervical ganglion, right ansae subclavia, left ansae subclavia, right stellate ganglion, left stellate ganglion, right paravertebral chain between T1-T6 ganglia, left paravertebral chain between T1-T6 ganglia, right paravertebral chain between T1-T4 ganglia, left paravertebral chain between T1-T4 ganglia, right paravertebral chain between T1-T2 ganglia and left paravertebral chain between T1-T2 ganglia.

The cardiac-related sympathetic nerve to be modulated (e.g. inhibited) is in either an afferent or an efferent neural circuit. When the invention refers to inhibition of more than one cardiac-related sympathetic nerves, the cardiac-related sympathetic nerves may be in: (a) an afferent neural circuit, (b) an efferent neural circuit, or (c) both afferent and efferent neural circuits. Where the invention refers to a modified cardiac-related sympathetic nerve m the extracardiac intrathoracic neural circuit, this nerve is ideally present in situ in a subject.

Inhibition of Neural Activity

According to the invention, inhibition results in neural activity in at least part of the cardiac-related sympathetic nerve in the extracardiac intrathoracic neural circuit being reduced compared to baseline neural activity in that part of the nerve. This reduction in activity can be across the whole nerve, in which case neural activity is reduced across the whole nerve.

As used herein, "neural activity" of a nerve means the signaling activity of the nerve, for example the amplitude, frequency and/or pattern of action potentials in the nerve.

The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

In some cases, the inhibition of neural activity may be a block of neural activity i.e. action potentials are blocked from travelling beyond the point of the block in at least a part of the cardiac-related sympathetic nerve in the extracardiac intrathoracic neural circuit. A block on neural activity is thus understood to be blocking neural activity from continuing past the point of the block. That is, when the block is applied, action potentials may travel along the nerve or subset of nerve fibers to the point of the block, but not beyond the point of the block. Thus, the nerve or subset of nerve fibers at the point of block is modified in that the nerve membrane is reversibly depolarized or hyperpolarized by an electric field, such that an action potential does not propagate through the modified nerve. Hence, the nerve or the subset or nerve fibers at the point of the block is modified in that it has lost its capacity to propagate action potentials, whereas the portions of the nerve or the subset of nerve fibers before and after the point of block have the capacity to propagate action potentials.

When an electrical signal is used with the invention, the block is based on the influence of electrical currents (e.g. charged particles, which may be one or more electrons in an electrode attached to the nerve, or one or more ions outside the nerve or within the nerve, for instance) on the distribution of ions across the nerve membrane.

At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in is normal state, wherein action potentials propagate from point to adjacent point along the axon, and which can be observed using conventional experimentation. One way of characterizing a block of neural activity is a distribution of potassium and sodium ions at one or more points in the axon which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization or hyperpolarization of the nerve membrane that would not otherwise occur. The depolarization or hyperpolarization of the nerve membrane caused by the temporary external electrical field blocks the propagation of an action potential across that point, because the action potential is unable to influence the distribution of potassium and sodium ions, which is instead governed by the temporary external electrical field. This is a nerve operating in a disrupted state, which can be observed by a distribution of potassium and sodium ions at a point in the axon (the point which has been blocked) that has an electrical membrane potential that is not influenced or determined by the electrical membrane potential of an adjacent point.

Block of neural activity encompasses full block of neural activity in the nerve, i.e. there is no neural activity in the whole nerve.

Blocking may be a partial block. Partial block may be such that the total signaling of a subset of nerve fibers of the nerve is partially reduced compared to baseline neural activity in that subset of fibers of the nerve. For example a reduction in neural activity of 5%, 10%, 15%, 20%, 25%, 30%, 35%, 40%, 45%, 40%, 50%, 60%, 70%, 80%, 90% or 95%, or blocking of neural activity in a subset of nerve fibers of the nerve. The neural activity may be measured by methods known in the art, for example, by the number of action potentials which propagate through the axon and/or the amplitude of the local field potential reflecting the summed activity of the action potentials.

The invention may selectively block nerve fibers of various sizes within a nerve. Larger nerve fibers tend to have a lower threshold for blocking than smaller nerve fibers. Thus, for example, increasing signal amplitude (e.g. increasing amplitude of an electric signal) may generate block of the smaller fibers.

Block of neural activity as described herein should not be confused with the clinical condition of "heart block", which typically occurs if the transmission of the pulse between the sinoatrial (SA) node, the atrioventricular (AV) node and the ventricles is interrupted.

Modulation (e.g. inhibition) of neural activity may be an alteration in the pattern of action potentials. It will be appreciated that the pattern of action potentials can be modulated without necessarily changing the overall frequency or amplitude. For example, modulation (e.g. inhibition) of the neural activity may be such that the pattern of action potentials is altered to more closely resemble a healthy state rather than a disease state.

Modulation (e.g. inhibition) of neural activity may comprise altering the neural activity in various other ways, for example increasing or decreasing a particular part of the neural activity and/or stimulating new elements of activity, for example: in particular intervals of time, in particular frequency bands, according to particular patterns and so forth.

One advantage of the invention is that modulation (e.g. inhibition) of the neural activity is reversible. Hence, the modulation (e.g. inhibition) of neural activity is not permanent. For example, upon cessation of inhibition, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible inhibition, the neural activity returns substantially fully to baseline neural activity. That is, the neural activity following cessation of inhibition is substantially the same as the neural activity prior to inhibition (e.g. prior to a signal being applied). Hence, the nerve or the portion of the nerve has regained its capacity to propagate action potentials.

In other embodiments, modulation (e.g. inhibition) of the neural activity may be substantially persistent. As used herein, "persistent" is taken to mean that the modulated (e.g. inhibited) neural activity has a prolonged effect. For example, upon cessation of inhibition, neural activity in the nerve remains substantially the same as when inhibition was occurring—i.e. the neural activity during and following inhibition is substantially the same. Reversible inhibition is preferred.

Inhibition of the neural activity may be (at least partially) corrective. As used herein, "corrective" is taken to mean that the inhibited neural activity alters the neural activity towards the pattern of neural activity in a healthy individual, and this is called axonal modulation therapy. That is, upon cessation of inhibition, neural activity in the nerve more closely resembles (ideally, substantially fully resembles) the pattern of action potentials in the cardiac-related sympathetic nerve in the extracardiac intrathoracic neural circuit observed in a healthy subject than prior to inhibition. Such corrective inhibition can be any inhibition as defined herein. For example, inhibition may result in a block on neural activity, and upon cessation of inhibition the pattern of action potentials in the nerve resembles the pattern of action potentials observed in a healthy subject. By way of further example, inhibition may result in neural activity resembling the pattern of action potentials observed in a healthy subject and, upon cessation of inhibition, the pattern of action potentials in the nerve remains the pattern of action potentials observed in a healthy subject.

By way of further example, inhibition may result in modulation such that cardiac-related sympathetic nerve in the extracardiac intrathoracic neural circuit neural activity resembles the pattern of action potentials observed in a healthy subject, and upon cessation of the signal, the pattern of action potentials in the nerve resembles the pattern of action potentials observed in a healthy subject. It is hypothesized that such a corrective effect is the result of a positive feedback loop—that is, the underlying disease state is treated as result of the claimed methods, and therefore the multi-modal sensory signals along the cardiac-related sympathetic nerve in the extracardiac intrathoracic neural circuit are not abnormal, and therefore the disease state is not perpetuated by the abnormal cardiac-related sympathetic nerve in the extracardiac intrathoracic neural circuit neural activity.

Treatment or Prevention of Cardiac Dysfunction

The invention is useful in treatment or prevention of cardiac dysfunction.

The invention is useful for treating or preventing any cardiac condition where the pathology is driven by sympatho-excitation. Cardiac rate, contractility, and excitability are known to be modulated by centrally mediated reflex pathways. The heart rate, spread of electrical activity on the heart and force of contraction is increased when the sympathetic nervous system is stimulated, and is decreased when the sympathetic nervous system is inhibited. This may also be accomplished when the parasympathetic nervous system is stimulated. Increased sympathetic tone is associated with various cardiac conditions, e.g. heart failure, myocardial infarction, hypertension and cardiac arrhythmias.

Heart failure is a condition caused by the heart failing to pump enough blood around the body to meet the demands of peripheral tissues. Heart failure may present itself as congestive heart failure (CHF) due to the accompanying venous and pulmonary congestion. Heart failure can be due to a variety of etiologies such as ischemic heart disease. Cardiac decompensation is typically marked by dyspnea (difficulty breathing), venous engorgement and edema, and each decompensation event can cause further long term deterioration of the heart function. Heart failure patients have reduced autonomic balance, typically with a sympathetic overdrive, which is associated with left ventricular dysfunction and increased mortality.

Myocardial infarction occurs when myocardial ischemia, a diminished blood supply to the heart, exceeds a critical threshold and results in irreversible myocardial cell damage or death.

The invention may relate to treating or preventing cardiac arrhythmia, also called cardiac dysrhythmia (or simply irregular heart beat), which refers to a group of conditions in which there is abnormal electrical activity in the heart. Some arrhythmias are life-threatening medical emergencies that can result in cardiac arrest and sudden death. Other cause symptoms such as an abnormal awareness of heart beat. Others may not be associated with any symptoms at all but predispose toward potentially life-threatening stroke, embolus or cardiac arrest. Cardiac arrhythmia can be classified by rate (physiological, tachycardia or bradycardia), mechanism (automaticity, re-entry or fibrillation) or by site of origin (ventricular or supraventricular).

Preferably, the invention relates to treating or preventing ventricular arrhythmia, e.g. ventricular tachycardia (VT) and ventricular fibrillation (VF). Ventricular arrhythmias are characterized by a disruption in the normal excitation-contraction rhythm of heart. In particular, VT and VF are characterized by abnormally rapid, asynchronous contraction of the ventricles. As such, the heart is unable to adequately pump oxygenated blood to the systemic circulation. If not treated immediately, ventricular arrhythmias can lead to additional tissue damage or patient death. These potentially life threatening events are characterized by, among other things, an increase in transient calcium currents and an elevation in diastolic calcium concentration in cardiac tissue, lengthening of the cardiac action potential, a drop in blood pressure and ischemia (lack of adequate blood flow to the heart). These changes can potentially affect the return of spontaneous circulation, hemodynamics, refibrillation and resuscitation success.

The inventors found that electric nerve block application during aberrant cardiac sympathetic stimulation is capable of stabilizing cardiac electrical and/or mechanical function. For example, Study 3 shows that when DC was delivered to the T1-T2 region during T3 stimulation, the increase in the chronotropic, dromotropic and inotropic functions in response to T3 stimulation was reduced during the period of DC delivery. Thus, electric nerve block (e.g. DC block) is effective in treating cardiac dysfunction, i.e. the electric nerve block can be used in a reactive manner. The invention can be configured as a closed-loop where the control of block is engaged automatically via one or more physiological sensors (described further below).

The inventors also found that electric nerve block application at the onset of aberrant cardiac sympathetic stimulation is capable of preventing cardiac dysfunction. For example, Study 3 shows that when DC was delivered at the onset of T3 stimulation, the increase in the chronotropic and inotropic functions in response to T3 stimulation was not achieved until after DC delivery was removed.

Interestingly, the percentages block of inotropic and chronotropic responses were highly effective for DC pre-emptive use, with at least 80% block for both inotropic and chronotropic responses. Thus, electric nerve block (e.g. DC block) is effective in preventing cardiac dysfunction, i.e. the electric nerve block can be used in a pre-emptive manner. The pre-emptive use can be configured as: (i) a closed-loop where the control of block is automatically via one or more physiological sensors (described further below); or (ii) an open-loop where the control of block is through a switch.

Assessing Cardiac Dysfunction

The invention may also involve detecting one or more signals from the subject indicative of cardiac function. This may be done before, during and/or after modulation (e.g. inhibition) of neural activity in a cardiac-related sympathetic nerve in the extra-cardiac intrathoracic neural circuit. The signal may be a physiological response indicated by assessing a biomarker indicative of cardiac dysfunction.

Thus the invention may involve assessing a biomarker indicative of cardiac dysfunction, which may be organ-based or neuro-based. An organ-based biomarker may be any measurable physiological parameter of the heart. For example, a physiological parameter may be one or more of the group consisting of: a chronotropic response, a dromotropic response, a lusitropic response and an inotropic response. Any of these parameters may be indicated by measuring the heart rate, heart rhythm and heart electromechanical coupling (e.g. ventricular pressure, ventricular contractility, activation-recovery interval, effective refractory period, stroke volume, ejection fraction, end diastolic fraction, stroke work, arterial elastance).

Chronotropic responses refer to changes in the heart rate and/or rhythm. These effects may be indicated using known techniques in the art, such as by electrocardiography, e.g. using the RR-interval.

Dromotropic responses refer to changes to the conduction speed in the atrioventricular (AV) node. These effects may be indicated using known techniques in the art, such as by electrocardiography, e.g. using the PR-interval which would indicate the electrical spread across the atria to the AV-node.

Lusitropic responses refer to the changes in the rate of myocardial relaxation. These effects may be indicated using known techniques in the art, such as by measuring the rate of pressure change in the ventricle (e.g. dP/dT).

Inotropic responses refer to the strength of contraction of heart muscle (i.e. myocardial contractility). These effects may be indicated using known techniques in the art, such as by measuring the rate of pressure change in the ventricle (e.g. dP/dT). Respiration parameters may also be useful. They can be derived from, for example, a minute ventilation signal and a fluid index can be derived from transthoracic impedance. For example decreasing thoracic impedance reflects increased fluid buildup in lungs, and indicates a progression of heart failure. Respiration can significantly vary minute ventilation. The transthoracic impedance can be totaled or averaged to provide an indication of fluid buildup.

Heart Rate Variability (HRV) a technique useful for assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and parasympathetic nerve activity.

The invention may involve assessing the heart rate by methods known in the art, for example, with a stethoscope or by feeling peripheral pulses. These methods cannot usually diagnose specific arrhythmias but can give a general indication of the heart rate and whether it is regular or irregular.

Not all of the electrical impulses of the heart produce audible or palpable beats; in many cardiac arrhythmias, the premature or abnormal beats do not produce an effective pumping action and are experienced as "skipped" beats.

The invention may also involve assessing the heart rhythm. For example, the simplest specific diagnostic test for assessment of heart rhythm is the electrocardiogram (abbreviated ECG or EKG). A Holter monitor is an EKG recorded over a 24-hour period, to detect arrhythmias that can happen briefly and unpredictably throughout the day.

Other useful assessment techniques include using a cardiac event recorder; performing an electrophysiological (EP) study or performing an echocardiogram.

The invention may involve assessing a neuro-based biomarker. Hence, in some embodiments, the physiological parameter may be one or more abnormal cardiac electrical signals from the subject indicative of cardiac dysfunction. The abnormal cardiac electrical signals may be measured in a cardiac-related intrathoracic nerve or peripheral ganglia of the cardiac nervous system. The abnormal electric signals may be a measurement of cardiac electric activity.

Example of assessing cardiac electrical signals include microneurography or plasma noradrenaline concentration. Microneurography involves using fine electrodes to record 'bursts' of activity from multiple or single afferent and efferent nerve axons [25,26]. The measurement of regional plasma noradrenaline spillover is useful in providing information on sympathetic activity in individual organs. Following nerve depolarization, any remaining noradrenaline in the synapse, the 'spillover', is washed out into the plasma and the plasma concentration is therefore directly related to the rate of sympathetic neuronal discharge [27,28,29].

Treatment of cardiac dysfunction can be assessed in various ways, but typically involves an improvement in one or more detected physiological parameters (e.g. one or more of the biomarkers mentioned above), i.e. the value of the parameter in the subject is changed towards the normal value or normal range for that value.

For an example, in a subject having cardiac dysfunction, an improvement in a measurable physiological parameter may be a decrease in a chronotropic, a dromotropic, a lusitropic and/or an inotropic response.

For example, a decrease in heart rate, conduction or heart contractility (e.g. ventricular pressure, ventricular contractility, activation-recovery interval, effective refractory period, stroke volume, ejection fraction, end diastolic fraction, stroke work, arterial elastance). The invention might not lead to a change in all of these parameters. Suitable methods for determining the value for any given parameter will be appreciated by the skilled person.

Therapy of cardiac dysfunction may be indicated by an improvement in the profile of neural activity in the cardiac-related sympathetic nerve. That is, treatment of the cardiac dysfunction is indicated by the neural activity in the cardiac-related sympathetic nerve approaching the neural activity of the resting state of the subject.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values are well known to the skilled person.

As used herein, a measurable physiological parameter is detected in a subject when the value for that parameter exhibited by the subject at the time of detection is determined. A detector is any element able to make such a determination.

In certain embodiments, the invention further comprises a step of detecting one or more physiological parameters of the subject, wherein the signal is applied only when the detected physiological parameter meets or exceeds a predefined threshold value. The physiological parameter may be any parameter described herein. This is useful for treatment or prevention of cardiac dysfunction.

In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulatory (e.g. neuroinhibitory) device/system, the device/system further comprises at least one detector configured to detect the one or more physiological parameters.

A "predefined threshold value" for a physiological parameter is the minimum (or maximum) value for that parameter that must be exhibited by a subject or subject before the specified intervention is applied. For any given parameter, the threshold value may be defined as a value indicative of a pathological state or a disease state, or as a value indicative of the onset of a pathological state or a disease state. Thus, depending on the predefined threshold value, the invention can be used as a prevention or a treatment. Alternatively, the threshold value may be defined as a value indicative of a physiological state of the subject (that the subject is, for example, asleep, post-prandial, or exercising). Appropriate values for any given parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that parameter than the predefined threshold value.

The invention is useful for subjects who are at risk of developing cardiac dysfunction may be subjected to application of the signals described herein, thereby decreasing the arrhythmic burden. The cardiac testing strategies for subjects at risk of cardiac dysfunction are known in the art, e.g. heart rate variability (HRV), baroreflex sensitivity (BRS), heart rate turbulence (HRT), heart rate deceleration capacity (HRDC) and T wave alternans (TWA). Deviation of these parameters from the baseline value range would be an indication of the subject being at risk of developing cardiac dysfunction.

Other indications include when the subject has a history of cardiac problems or a history of myocardium injury. For example, the subject has undergone heart procedures, e.g. heart surgery. The subject may have had a myocardial infarction. The subject may have emphysema or chronic obstructive pulmonary disease. The subject may have a history of arrhythmia or is genetically pre-disposed to arrhythmia For preventive use, a subject at risk of developing cardiac dysfunction may be subjected to signal application for x min at regular intervals, wherein x=≤3 min, =≤5 min, =≤10 min, =≤20 min, =≤30 min, =≤40 min, =≤50 min, =≤60 min, =≤70 min, =≤80 min, =≤90 min, =≤120 min, or =≤240 min. The interval may be once every day, once every 2 days, once every 3 days etc. The interval may be more than once a day, e.g. twice a day, three times a day etc.

A subject suitable for the invention may be any age, but will usually be at least 40, 45, 50, 55, 60, 65, 70, 75, 80 or 85 years of age.

The invention can be used in combination with conventional anti-arrhythmia therapies. For example, some arrhythmias, e.g. atrial fibrillation, cause blood clotting within the heart and increase risk of embolus and stroke. Anticoagulant medications such as warfarin and heparin, and anti-platelet drugs such as aspirin can reduce the risk of clotting. Thus, the invention can be used in combination with administering an anticoagulant. The invention also provides an anticoagulant medicine for use in treating a subject, wherein the subject has an implanted device/system of the invention in signaling contact with a cardiac-related sympathetic nerve in the extracardiac intrathoracic neural circuit.

An Implantable Device/System for Implementing the Invention

An implantable device according to the invention comprises at least one transducer, preferably an electrode, suitable for placement on or around a cardiac-related sympathetic nerve in the extracardiac intrathoracic neural circuit. The device/system preferably also comprises a controller coupler to the at least one transducer. The various components are preferably part of a single physical device. As an alternative, however, the invention may use a system in which the components are physically separate, and communicate wirelessly. Thus, for instance, the transducer and the controller can be part of a unitary device, or together may form a system (and, in both cases, further components may also be present to form a larger device or system e.g. a power source, a sensor, etc.).

Electrodes

Electrodes capable of controlling delivery of current to a nerve cell in order to affect the signals passing along the nerve fiber are known in the art [30]. Reference discloses several types of electrode for non-damaging neural tissue conduction block. The document discloses cuff electrodes (e.g. spiral cuff, helical cuff or flat interface), and flat interface electrodes, both of which are also suitable for use with the present invention. A mesh, a linear rod-shaped lead, paddle-style lead or disc contact electrode (including multi-disc contact electrodes) are also disclosed in and would be suitable for use in the present invention. Also suitable are intrafascicular electrode, glass suction electrode, paddle electrode, bipolar hemi-cuff electrode, bipolar hook electrode, percutaneous cylindrical electrode. Electrodes may be monopolar, bipolar, tripolar, quadripolar or have five or more poles. The electrodes may fabricated from, or be partially or entirely coated with, a high charge capacity material such as platinum black, iridium oxide, titanium nitride, tantalum, poly(elthylenedioxythiophene) and suitable combinations thereof.

Reference discloses separated-interface nerve electrodes, and in particular forms of ionic coupling electrodes (for example in the form of a cuff electrode) that facilitates the application of a prolonged single phase current to a nerve which mitigates the kind of nerve damage described elsewhere herein. This kind of electrode would be suitable for use in the present invention.

Reference discloses adjustable nerve electrodes, particularly suited for nerve block by delivery of high frequency alternating current (HFAC). The electrodes comprises two or more contacts and logic configured to control, optionally selectively control, the application of HFAC signals through the two or more contacts, in order to control onset response. This kind of electrode would also be suitable for use in the present invention, particularly in combination with delivery of a HFAC or KHFAC signal.

In the examples disclosed elsewhere herein, certain types of electrode have been used for controlling delivery of specific types of signal. In one example described in more detail below, silver wires were placed around a cardiac-related sympathetic nerve in the extracardiac intrathoracic neural circuit (specifically the T1-T2 paravertebral chain) and when connected to an AC signal generator they were found to be effective for controlling delivery of a KHFAC signal (kilohertz frequency alternating current). In another example described in more detailed below, a 4-node carbon black coated platinum electrode was placed underneath or around a cardiac-related sympathetic nerve in the extracardiac intrathoracic neural circuit (specifically the T1-T2 segment) and when connected to individual DC current sources was found to be effective for controlling delivery of a DC signal, in particular a charge-balanced DC signal.

The transducer (e.g. signal electrode) is configured to be placed near, attached to or implanted within the nerve. In some embodiments, the transducer is attached to the nerve such that it partially or fully circumvents the nerve. Preferably, the transducer circumvents the nerve by an angle of at least 180°.

More preferably, the transducer circumvents the nerve by at an angle of at least 270°. Put another way, the transducer preferably circumvents at least 50% of the circumference of the nerve, and even more preferably at least 75% of the nerve. In such embodiments, the transducer may circumvent the nerve by an angle of one of: 180°, 210°, 240°, 270°, 300°, 330°, and 360°. According to [33], increasing the contact between the nerve and the transducer leads to an improved mitigation of the onset response.

The at least one transducer (e.g. at least one electrode) may attach unilaterally or bilaterally to the cardiac-related sympathetic nerve or nerves in the extracardiac intrathoracic neural circuit. The at least one transducer may attach at a single point or at multiple points, either on a single nerve or multiple nerves. For example, the at least one transducer may attach at a single point or at multiple points on the left side and/or on the right side. The multiple points may be at the same site in a cardiac-related sympathetic nerve in the extracardiac intrathoracic neural circuit. In this embodiment, the multiple points may be positioned on the nerve: S1 0 mm apart. Alternatively, the multiple points may be at different sites in the same cardiac-related sympathetic nerve in the extracardiac intrathoracic neural circuit. In this case, the sites may be mm apart, wherein y≥1 mm, ≥2 mm, ≥3 mm, ≥4 mm, ≥5 mm, ≥6 mm, ≥7 mm, ≥8 mm, ≥9 mm. Alternatively, y may be ≥10 mm, ≥20 mm or ≥30 mm. In one embodiment, the sites may be ≤10 mm apart, in particular where the at least one electrode attaches unilaterally. For example, modulation (e.g. inhibition) may take place at multiple points in the region between the T1-T4, optionally T1-T2 paravertebral chain and/or the ansae subclavia. The multiple points may be in different cardiac-related sympathetic nerves in the extracardiac intrathoracic neural circuits. For example, the inhibition may take place at both the ansae subclavia, e.g. as demonstrated in Studies 1-4.

For an AC signal, the device may use a single phase signal, and therefore provide a single signal electrode, with a ground electrode provided either near, attached to or implanted within the nerve (i.e. in close proximity to the signal electrode) or remote from, even external to the subject. Alternatively, the device may comprise a biphasic signal, wherein two signal electrodes are provided 180° out of phase, both placed near, attached to or implanted within the nerve and in close proximity to each other.

For a DC signal, one or more signal electrodes may be provided. The electrodes may be bipolar and placed (e.g.) either side of a nerve or otherwise in close proximity, in which case the DC current may flow between the electrodes. Alternatively, the electrodes may be monopolar, in which case the DC current may flow from the signal electrode to a remote ground electrode provided either near, attached to or implanted within the nerve (i.e. in close proximity to the signal electrode) or remote from, even external to the subject.

In certain embodiments, an onset response may be reduced by an adjusting the attributes of the electrode. In particular, the electrode may be adjusted by changing geometric attributes including, but not limited to, the number of electrodes, the width of the electrodes, the orientation of the electrodes, the distance between two or more electrodes, the surface area of the electrodes, and radial distance from the nerve axis. This is discussed in [34]. These geometric attributes may not necessarily require a physical adjustment, the geometric attributes may be adjusted electronically according to the method and system proposed in [34]. To this end, the invention may include one or more remote electrical switches for adjustment of the geometric attributes.

In certain embodiments, an onset response may be reduced by adjusting the width of the electrode in contact with the nerve or, for a biphasic signal, adjusting the distance between two electrodes in contact with the nerve, where the width of the electrode and distance between two electrodes are defined in the direction along the nerve axis. In particular, increasing the width of the electrodes and/or reducing the distance between two electrodes in contact with the nerve reduces the onset response. These electrode geometries are optimized to depolarize the fibers in a nerve to a blocked state with minimal current, thus resulting in a reduced onset response, as discussed in [33,34].

A specific form of electrode (referred to herein as a carousel electrode) is disclosed in [35]. The electrode has multiple electrode contacts for contacting the nerve. In one embodiment, four contiguous monopolar electrode contacts is provided. As described in that document, the carousel electrode is operated by continuously cycling DC pulses across the plurality of electrode contacts. The application of a signal using a carousel electrode is described below.

Where it is desired to mask the onset response of an AC signal (such as a KHFAC signal), for instance by providing a DC signal (such as a DC ramp), during which the AC signal commences, it is possible to provide a hybrid electrode comprising one or more nodes for providing the AC signal and one or more nodes for providing the DC signal. In such a case, each signal may be provided to the hybrid electrode from a separate power source.

Suitable Forms of an Electrical Signal

Signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the cardiac-related sympathetic nerve in the extracardiac intrathoracic neural circuit (or fibers thereof, or other nerve tissue to which the signal is applied) to conduct action potentials when application of the signal ceases, even if that conduction is in practice inhibited or blocked as a result of application of the non-destructive signal.

The signal will usually be an electrical signal, which may be, for example, a voltage or current. In certain such embodiments the signal applied comprises a direct current (DC), such as a charge balanced direct current, or an alternating current (AC) waveform, or both a DC and an AC waveform. Characteristics of inhibitory electrical waveforms for use with the invention are described in more detail below. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. However, electrical signals are just one way of implementing the invention, and other suitable signals are described below.

A combination of charge balanced DC and AC is particularly useful for mitigating the onset response that is typical of AC, particularly KHFAC signals. In these cases, a ramp DC signal, which does not induce an onset response, is applied for a short initial period to block the nerve, during or after which an AC signal is introduced (e.g. see [36]). Reference discloses an onset-mitigating high frequency nerve block, wherein a ramped DC nerve block signal is applied to the nerve, followed by application of a HFAC nerve block. Such a signal may be used with the present invention, in particular with a hybrid electrode, as described above.

A particular pattern of signals suitable for mitigating onset is a signal having a DC ramp followed by a plateau and charge-balancing; followed by a first AC waveform, wherein the amplitude of the waveform increases during the period the waveform is applied; followed by a second AC waveform having a lower frequency and/or lower amplitude than the first waveform.

In certain embodiments, the signal is a kilohertz frequency alternating current (KHFAC) signal, a charge balanced direct current carousel (CBDCC) signal, or a hybrid thereof. In some embodiments, the waveform comprises a kilohertz frequency alternating current (KHFAC) waveform, a charge balanced direct current carousel (CBDCC) waveform, or a hybrid thereof.

Conduction block using electrical signals (e.g. AC and DC signals) is produced by creating a finite region, optionally of axons, through which action potentials cannot pass. This region is positioned directly under the electrode and generally extends longitudinally a few millimeters. Thus, the block effect is isolated to the immediate vicinity of the blocking electrode, with no systemic effects.

A unique characteristic of the block is the rapid reversibility of the block when the signal is terminated. This reversibility is clearly demonstrated in the examples where the cardiac responses return to the pre-block values.

A few hypotheses have been put forward for the mechanism by which these electrical signals block nerve conduction [30]. One early explanation was the accumulation of extracellular potassium. The second more recent proposal has been that outward potassium currents overwhelm the inward sodium currents at the nodes or axon section (in unmyelinated axons) influenced by the KHFAC and produce block. The third hypothesis has recently gained traction and it focuses on sodium channel inactivation as the cause of KHFAC block. Animal model studies demonstrated that KHFAC resulted in an increased inward sodium current compared to the outward potassium current, leading to a dynamic membrane depolarization of a number of nodes under the electrode. This depolarization led to the inactivation of about 90% of the sodium channels in the node directly under the electrode. Regardless of the mechanism, application of electrical signals are effective in blocking neural activity.

In certain embodiments the DC waveform or AC waveform may be a square, sinusoidal, triangular, sawtooth or complex waveform. The DC waveform may alternatively be a constant amplitude waveform. In certain embodiments the electrical signal is an AC sinusoidal waveform.

The electric signal may be applied as step change or as a ramp change in current or intensity.

It will be appreciated by the skilled person that the current amplitude of an applied electrical signal necessary to achieve the intended neuromodulation (e.g. neuroinhibitory) will depend upon the positioning of the electrode and the associated electrophysiological characteristics (e.g. impedance). It is within the ability of the skilled person to determine the appropriate current amplitude for achieving the intended neuromodulation (e.g. neuroinhibitory) in a given subject. For example, the skilled person is aware of methods suitable to monitor the neural activity profile induced by neuroinhibition.

Notwithstanding the specific examples mentioned above, both AC and DC signals are found to be suitable for bringing about the invention. In the case of AC signals, it has been found that KHFAC signals are capable of creating a block in a cardiac-related sympathetic nerve in the extracardiac intrathoracic neural circuit, and an implantable device configured to generate KHFAC signals is therefore contemplated, a specific example of which is given below in 'Example 1'. Further details of the utilization of KHFAC signals in nerve conduction is found in [30].

However, as explained elsewhere herein, the use of KHFAC signals causes a problem known as transient sympatho-excitation at onset. One solution to the onset problem may be found by using DC signals, and an implantable device configured to generate DC signals is therefore contemplated, a specific example of which is given below. The importance of charge balancing to avoid adverse long-term effects of DC is described in [38,35] and elsewhere, and includes factors such as nerve damage from the creation of free radicals, pH shift, accumulation of ionic charges around the electrodes, and erosion of the electrode material. 'Example 2' below is configured to apply a charge-balanced DC signal. Moreover, DC signals can have lower power requirements.

However, a constraint exists in the use of a charge-balanced DC signal in that the maximum duration of the pulse that depolarizes the cell membrane to initiate an action potential (referred to in and as the cathodal phase) is limited by adverse effects mentioned above, which are a function of both pulse duration and signal amplitude. Of course, the maximum duration of a single DC pulse that can be applied without significant adverse effects may be insufficient to be effective for practising the invention; in other words, the block applied by the cathodal phase of a single charge-balanced DC pulse that does not cause significant adverse effects does not last long enough to be of use. As disclosed in [35], this problem may be addressed by using a DC 'carousel' electrode (mentioned above), whereby a plurality of electrode contacts spaced apart along the length of the DC carousel electrode apply a cycle of a plurality of charge balanced DC pulses, each new pulse applied by an electrode contact being temporally offset from the previous pulse that was applied to the adjacent node. Using a charged-balanced DC carousel enables a continuous neural block along a region of an axon without damaging the axon. 'Example 2' below uses a DC carousel electrode.

The following examples describe devices configured to deliver particular kinds of AC and DC signals introduced above, and the components of the device used to do so. The devices also have additional components, such as a microprocessor, power source, memory, and so on, which are described in more detail below.

Electrode Example 1—Devices Configured to Deliver KHFAC

An electrode formed of silver wires is provided and connected to an AC signal generator on the implantable device. Although silver wire is used here, any suitable electrode may be used, as described above. In this case, the electrode comprises at least one anode and at least one cathode formed of silver wires. The AC signal provided by the signal generator is in this case (though need not be) a biphasic square wave, wherein the signal delivered to the at least one anode is 180° out of phase with the signal delivered to the cathode. Alternatively, the AC signal provided by the signal generator is a biphasic sawtooth wave, such as in [39]. The AC signal provided by the signal generator may alternatively be a sine wave.

In one example, the selected frequency of an AC signal provided by the AC signal generator and effective for producing a KHFAC block to the ansae subclavia (see FIG. 2C and associated description elsewhere herein) is 5 kHz, and the selected voltage is 16 volts. The implantable device may be configured to deliver only this frequency and/or voltage, or may be configured to deliver signals within certain bounds of the above-stated frequency and/or voltage. The frequency may be between 6 and 26 kHz, preferably between 8 and 24 kHz, more preferably between 10 and 22 kHz, still more preferably between 12 and 20 kHz, still more preferably between 14 and 18 kHz. The voltage may be between 10 and 30 volts, preferably between 12 and 28 volts, more preferably between 14 and 26 volts, still more preferably between 16 and 24 volts, still more preferably between 18 and 22 volts.

In one example, the selected frequency of the AC signal provided by the AC signal generator and effective for producing a KHFAC block to the ansae subclavia (see FIG. 3 and associated description elsewhere herein) is 5 kHz, and the selected voltage is 15 volts. The implantable device may be configured to deliver only this frequency and/or voltage, or may be configured to deliver signals within certain bounds of the above-stated frequency and/or voltage. The frequency may be between 5 and 25 kHz, preferably between 7 and 23 kHz, more preferably between 9 and 21 kHz, still more preferably between 11 and 19 kHz, still more preferably between 13 and 17 kHz. The voltage may be between 5 and 25 volts, preferably between 7 and 23 volts, more preferably between 9 and 21 volts, still more preferably between 11 and 19 volts, still more preferably between 13 and 17 volts.

Electrode Example 2—Devices Configured to Deliver Charged Balanced DC Carousel

A 4-node charge balanced DC 'carousel' electrode (i.e. a carousel electrode with four electrode contacts) is shown in FIG. 10, the electrode being made from platinum and coated with carbon black. A DC source, provided on the implantable device, is electrically connected to each electrode contacts of the 4-node electrode.

The electrode nodes are spatially separated from each other but aligned along a common axis which, when implanted, is parallel with the axis of the nerve fibers. In this iteration, the electrode has the following dimensions—1 cm×1 cm, each node being 1.8 mm and separated from next node by 1 mm Each node of the electrode has the same dimension measured along the axis, and preferably also has the same dimension perpendicular to the axis. The nodes are evenly spaced on the electrode. Electrode dimensions are scalable and in other iterations, dimensions can be increased or decreased depending on size of nerve to which the electrode with be placed.

In combination with a microprocessor (described in more detail below), each DC source is capable of generating a charge-balanced biphasic pulse waveform. FIG. 10B shows an example of a charge-balanced biphasic pulse and the trace in FIG. 10C and at the top of FIG. 11 shows four such pulses, shifted in time as described below. The waveform comprises a cathodic phase that produces a nerve block, and an anodic 'recharge' phase that delivers overall (net) neutrality to prevent nerve damage from charge build up. The pulse begins at to at which point the current delivered to the node on the electrodes is zero (i=0;). The pulse then provides a negative (cathodic) pulse component at a cathodic current is (that produces a nerve block). The cathodic pulse component has a duration t1. The pulse then provides a positive (anodic) pulse component at an anodic current is (the recharge phase). The anodic pulse component has a duration t2. The pulse then returns to deliver a zero current (i.e. returning to i=0) lasting for duration t3, before reaching the end of the pulse, also known as the interpulse interval. The pulse is charge-balanced because the total charge (a function of pulse amplitude and time) delivered by the cathodic pulse component matches that delivered by the anodic pulse component, leaving no residual charge at the end of the pulse.

References [40, 41, 42] disclose other charge-balanced biphasic signals for producing a nerve block. In [41], the pulse width has a duration which is less than half of the period (i.e. I/frequency). With a pulse width of this duration, the hyperpolarization phase will be shorter in duration than the depolarizing phase, which leads to a reduction in the onset response. A reduction in onset response is desirable in the present invention. Thus, in certain embodiments, the signal has a pulse with having a duration which is less than half of I/frequency.

The cathodic phase of a suitable a charge-balanced biphasic pulse waveform comprises: (i) a 'ramp-to-plateau' phase during which the current changes from i=O to the cathodic current $i_c$; (ii) a 'plateau' phase at the cathodic current $i_c$; and (iii) a 'ramp to recharge' phase during which the current changes from the cathodic current $i_c$ to the anodic current $i_a$.

The microprocessor and DC source are configured to ramp the signal from zero to the cathodic current, and from the cathodic current to the anodic current (and optionally from the anodic current to zero). The rate of change of current (i.e. the slope of the ramp) is such that the pulses do not invoke an onset response in the nerve, as described elsewhere herein. Reference describes the importance of slow current ramps, and indicates ramps and plateaus (for both cathodic/block plateau and anodic/recharge phases) of the order of 1-3 seconds but without giving specific values. In their paper 'Characterization of high capacitance electrode for the application of direct current electrical nerve block' [43], Vrabec, et al. suggests a various charge-balanced biphasic DC signal waveforms. Two such waveforms have protocols wherein the 'ramp-to-plateau' and 'ramp-to-recharge' phases are both 2 second duration, and wherein the DC plateau is 2 seconds or 4 seconds duration, respectively (i.e. 2-2-2, and 2-4-2). This paper also discloses a CBDC waveform protocol used to block the onset from a KHFAC signal, wherein the 'ramp-to-plateau' phase has duration of 4 seconds, the DC plateau has a duration of 7 seconds and the 'ramp-to-recharge' phase has a duration of 2 seconds.

In the amplitude and duration of the anodic/recharge phase is indicated to be similar to the amplitude and duration of the cathodic/block phase, although no specific value are given. In Vrabec, et al., an in vitro test with a cathodic pulse (block) of 10 seconds duration followed by an anodic pulse (recharge) of 100 seconds duration with current amplitude of 10% of the amplitude of the cathodic pulse (to provide charge balance). A second example having a cathodic waveform protocol of 2-4-2 provided an anodic pulse (recharge) with current amplitude of 10% of the amplitude of the cathodic pulse. The duration of the anodic pulse in this example has a duration approaching 40 seconds, again to provide charge balance.

In the present invention, different CBDC waveform protocols have been shown to be effective. In the application of a CBDC signal to the ansae subclavia in a reactive manner (see FIG. 8A and associated description elsewhere herein), a 4-10-2 protocol was utilized with a cathodic current of 6 mA and an anodic current of 0.6 mA. In the application of CBDC current to the ansae subclavia in a pre-emptive manner (see FIG. 8B and associated description elsewhere herein), a 4-7-2 protocol was utilized with a cathodic current of 6 mA and an anodic current of 0.6 mA. Cathodic current values of between 0.5 mA and 6 mA, in particular 1 mA, 2 mA, 3 mA, 4 mA and 5 mA are possible, and have been tested (see FIGS. 8C, 8D, 9A-B and associated description elsewhere herein).

In the application of a CBDC signal to the T1-T2 paravertebral chain ganglion (FIG. 11B, FIG. 12 and associated description elsewhere herein), a 2-4-2 protocol was utilized with a cathodic current of 0.5-4 mA.

In these examples, which utilize a 4-node CBDC carousel electrode, the anodic current is selected such that the duration of the anodic (recharge) pulse is equal to or less than 3× the duration of the cathodic pulse. In this way, the CBDC waveform at the first node has completed its anodic (recharge) phase and is ready to begin its next cathodic (block) phase after the second, third and fourth nodes have completed their cathodic (block) phases, and so on as the carousel cycles through the nodes. In other words, for a cathodic pulse of 2-4-2 protocol (e.g. 2 seconds 'ramp-to-plateau', 4 seconds 'DC plateau' and 2 seconds 'ramp-to-recharge'), the maximum duration of the anodic pulse is 24 seconds (FIG. 10B). For the DC signals to be charge-balanced, therefore, the anodic current is preferably no less than one third the cathodic current (FIG. 10B). In the example of the application of a CBDCC signal to the T1-T2 paravertebral chain ganglion shown in FIG. 11, which has a cathodic current of 2.5 mA, the anodic current is preferably no less than 0.833 mA.

In combination with the microprocessor, the DC sources are temporally offset and operate as a DC carousel. A single cycle of the carousel comprises the plurality of DC sources sequentially providing their respective nodes with a pulse as described above, shifted in time. In a charge balanced DC carousel electrode therefore, a first cycle begins when the first DC source begins generating a first pulse in a cycle for application to the first node, after which the second DC source will generate a second pulse in the cycle for application to the second node, after which the third DC source will generate a third pulse in the cycle for application to the third node, after which the fourth DC source will generate a fourth pulse in the cycle for application to the fourth node, after which the first cycle ends. Once the first cycle has ended, the second repeats as the first. The effect of the four signals applied by the carousel electrode is to apply a substantially constant DC charge to the nerve (see trace FIG. 10C and FIG. 11) but without a corresponding charge imbalance.

Theoretically, a minimum of 2 nodes is required for CBDCC, although more could be provided, as long as the periodicity of the signals applied by the nodes is compensated accordingly. However, to implement the present invention, a minimum of 4 nodes and preferably exactly 4 nodes, is preferred.

Because each of the nodes on a DC carousel is driven by its own DC source, and the efficacy of the block is current dependent, the current delivered to each node can be tuned as necessary to adjust the current delivered to the nerve, and thus the block applied to each part of the nerve contacting the nodes.

Thus, a DC carousel electrode may comprise multiple nodes for DC current application, wherein each node is sequentially controlled in serial or random sequence. The current applied to a node of the DC carousel electrode may be applied as charged balanced waveform.

Other Suitable Forms of Transducer and Signal

The signal may comprise an ultrasonic signal. In certain such embodiments, the ultrasonic signal has a frequency of 0.5-2.0 MHz, optionally 0.5-1.5 MHz, optionally 1.1 MHz. In certain embodiments, the ultrasonic signal has a density of 10-100 W/cm 2 for example 13.6 W/cm 2 or 93 W/cm 2.

Another mechanical form of neuromodulation (e.g. neuroinhibition) uses ultrasound which may conveniently be implemented using external instead of implanted ultrasound transducers.

The signal may comprise an electromagnetic signal, such as an optical signal. Optical signals can conveniently be applied using a laser and/or a light emitting diode configured to apply the optical signal. In certain such embodiments, the optical signal (for example the laser signal) has an energy density from 500 mW/cm 2 to 900 W/cm 2 In certain alternative embodiments, the signal is a magnetic signal. In certain such embodiments, the magnetic signal is a biphasic signal with a frequency of 5-15 Hz, optionally 10 Hz. In certain such embodiments, the signal has a pulse duration of 1-1000 µs, for example 500 µs.

The signal may use thermal energy, and the temperature of a nerve can be modified to inhibit propagation of neurosignaling. For example, Patberg et al. discuss how cooling a nerve blocks signal conduction without an onset response, the block being both reversible and fast acting, with onsets of up to tens of seconds. Heating the nerve can also be used to block conduction, and is generally easier to implement in a small implantable or localized transducer or device, for example using infrared radiation from laser diode or a thermal heat source such as an electrically resistive element, which can be used to provide a fast, reversible, and spatially very localized heating effect (e.g. [45]). Either heating, or cooling, or both could be conveniently provided in vivo using a Peltier element. Where the signal applied to a nerve is a thermal signal, the signal can reduce the temperature of the nerve. In certain such embodiments the nerve is cooled to 14° C. or lower to partially inhibit neural activity, or to 6° C. or lower, for example 2° C., to fully inhibit neural activity. In such embodiments, it is preferably not to cause damage to the nerve. In certain alternative embodiments, the signal increases the temperature of the nerve. In certain embodiments, neural activity is inhibited by increasing the nerve's temperature by at least 5° C., for example by 5° C., 6° C., 7° C., 8° C., or more. In certain embodiments, signals can be used to heat and cool a nerve simultaneously at different locations on the nerve, or sequentially at the same or different location on the nerve.

In [34], inhibiting propagation of neurosignaling by cooling the nerve may also reduce the onset response. Accordingly, cooling may be used in the present invention combination with the DC and HFAC embodiments described above. To this end, the device/system of the present invention may comprise at least one transducer comprising a cooling element. The cooling element may take the form of a Peltier element provided in vivo.

The signal may use microwave signal to heat magnetic nanoparticles that absorb RF radiation, thereby heating surrounding tissue. A technique involving combining magnetic nanoparticles with proteins known to bind to specific protein targets on neural cell membranes.

Microprocessor

The implantable device may comprise a microprocessor. The microprocessor may be responsible for triggering the beginning and/or end of the signal delivered to the cardiac-related sympathetic nerve in the extracardiac intrathoracic neural circuit by the at least one transducer. Optionally, the microprocessor may also be responsible for generating and/or controlling the parameters of the signal.

The microprocessor may be in electrical communication with the signal generator, and the microprocessor may trigger the beginning and/or end of the signal delivered to the cardiac-related sympathetic nerve by communicating with the signal generator. An exemplary pulse generator with a processor configuration suitable for nerve stimulation applications is disclosed in ref.14.

The microprocessor may be configured to operate the device/system in an open-loop fashion, wherein a predefined signal (e.g. as described above) for treatment or prevention is delivered to a cardiac-related sympathetic nerve in the extracardiac intrathoracic neural circuit at a given periodicity (or continuously) and for a given duration (or indefinitely) without any external trigger, control or feedback mechanism. Alternatively, the microprocessor may be configured to operate the device/system in a closed-loop fashion, wherein a signal is applied based on an external trigger, control or feedback mechanism.

The microprocessor of the device may be constructed so as to generate, in use, a preconfigured and/or user-selectable signal that is independent of any input. Preferably, however, the microprocessor is responsive to an external signal, more preferably information pertaining to a physiological response in the subject.

As is well known, and described elsewhere herein, implantable cardioverter defibrillator (ICD) devices are known to be configured to detect physiological signals indicative of cardiac dysfunctions and abnormal heart rhythms, and upon detection perform one or more therapies including cardioversion, defibrillation and pacing of the heart. Indicative physiological signals include a decrease in ventricular pressure, a decrease in ventricular contractility, a decrease in heart rate, a decrease in activation-recovery interval and prolonged effective refractory period. An exemplary ICD device which monitors cardiac electrical activity, recognizes ventricular fibrillation and ventricular tachyarrhythmias with a sinusoidal wave form, and then delivers corrective defibrillatory discharges is disclosed in [46].

The implantable device of the present invention may comprise circuitry similar to that found in an ICD to detect physiological signals indicative of cardiac dysfunctions and abnormal heart rhythms, and use these signals to trigger the microprocessor to communicate to the signal generator to deliver a signal of the kinds described above (for example in Examples 1 and 2 above) to the cardiac-related sympathetic nerve in the extracardiac intrathoracic neural circuit using the at least one transducer.

The circuitry may comprise one or more sensors placed on parts of the body to detect physiological signals. These may include one or more electrodes placed on or around one or more ventricles of the heart to detect electrical activity; pressure and/or spatial sensors placed within a ventricle and configured to measure ventricular pressure, conduction and/or contractility.

Upon receipt of signals received from the one or more sensors, the processor may calculate the current heart rhythms, including heart rate, activation-recovery interval and effective refractory period, in accordance with techniques known in the art.

The device may comprise memory for storing physiological data pertaining to a normal heart rhythm. The data may be specific to the patient into which the device is implanted, and gleaned from various tests known in the art. Upon receipt of signals received from the one or more sensors, or else periodically or upon demand, the processor may compare the signals received from the one or more sensors with the physiological data stored in the memory and determine whether the received signals are indicative of a cardiac dysfunction or abnormal heart rhythm. The device may be configured such that if and when a cardiac dysfunction or abnormal heart rhythm is indicated, the processor communicates to the signal generator, and the signal generator triggers delivery of a signal to the cardiac-related sympathetic nerve in the extracardiac intrathoracic neural circuit by the at least one transducer.

A device according to the invention configured to operate in a closed-loop fashion may be configured to apply one or both of a pre-emptive block or a reactive block (by contrast, a device configured to operate in an open-loop fashion is configured to apply a pre-emptive block only).

In a device configured to operate in a closed-loop fashion, a pre-emptive block may be applied when the signals received by the one or more sensors are indicative of a cardiac dysfunction or abnormal heart rhythm that has yet to initiate. Once such signals are detected and compared with stored data (as described above), the processor may be configured to communicate to the signal generator to deliver a signal to the cardiac-related sympathetic nerve in the extracardiac intrathoracic neural circuit by the at least one transducer in advance of the initiation of the cardiac dysfunction or abnormal heart rhythm.

In a device configured to operate in an open-loop fashion, a reactive block may be applied when the signals received by the one or more sensors are indicative of a cardiac dysfunction or abnormal heart rhythm that is taking place. Once such signals are detected and compared with stored data (as described above), the processor may be configured to communicate to the signal generator to deliver a signal to the cardiac-related sympathetic nerve in the extracardiac intrathoracic neural circuit by the at least one transducer during the cardiac dysfunction or abnormal heart rhythm (see FIG. 8A and associated description elsewhere herein).

As an alternative to the sensing circuitry similar of an ICD which detects cardiac electrical activity indicative of cardiac dysfunctions and abnormal heart rhythms, a device according to the invention that operates in a closed-loop fashion could include circuitry that senses a neural activity in a cardiac-related sympathetic nerve or ganglia in the extracardiac intrathoracic neural circuit. The sensing circuitry may comprise one or more transducers, preferably electrodes, of any of the kinds described above that are suitable for sensing neural activity, as known in the art.

In response to neural activity, the processor may determine whether the received signals are indicative of a cardiac dysfunction or abnormal heart rhythm and, if and when a cardiac dysfunction or abnormal heart rhythm is indicated, the processor may communicates to the signal generator, and the signal generator trigger delivery of a signal to the cardiac-related sympathetic nerve in the extracardiac intrathoracic neural circuit by the at least one transducer.

As an alternative, or in addition, to the device's ability to respond to sensed physiological signals, the processor may communicate to the signal generator, and the signal generator may be triggered, upon receipt of a signal generated by a physician or by the subject in which the device is implanted. To that end, the implantable device may be part of a system comprising subsystems external to the subject, and including, for instance, a controller. An example of such a system is described below.

The controller may be configured to communicate to the signal generator to apply a signal to the cardiac-related sympathetic nerve in the extracardiac intrathoracic neural circuit intermittently or continuously. Suitable signals for use with the invention are discussed above. Intermittent inhibition involves applying the modulation (e.g. inhibition) in an (on-off)n pattern, where n>1. For instance, modulation (e.g. inhibition) can be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus inhibition is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods.

In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d. Intermittent inhibition may also be referred to as periodic inhibition, where the periodic pattern is the on-off pattern described above. Intermittent inhibition may be thought of as temporally selective treatment of cardiac dysfunction according to the on-off pattern.

In certain embodiments, modulation (e.g. inhibition) is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, modulation (e.g. inhibition) is applied continuously for the specified amount of time. In certain alternative such embodiments, modulation (e.g. inhibition) may be applied discontinuously across the day, provided the total time of application amounts to the specified time.

Continuous modulation (e.g. inhibition) may continue indefinitely, e.g. permanently. Alternatively, the continuous application may be for a minimum period, for example the signal may be continuously applied for at least 5 days, or at least 7 days.

Where modulation (e.g. inhibition) is controlled by a device/system of the invention, and where a signal is continuously applied to the nerve, although the signal might be a series of pulses, the gaps between those pulses do not mean the signal is not continuously applied.

In certain embodiments, modulation (e.g. inhibition) is applied only when the subject is in a specific state e.g. only when the subject is awake, only when the subject is asleep, prior to and/or after the ingestion of food, prior to and/or after the subject undertakes exercise, etc.

These various embodiments for timing of modulation (e.g. inhibition) can all be achieved using the controller, preferably external controller, in a device/system of the invention. In one embodiment, the controller is an external controller.

Other Components of the Implantable Device

The implantable device may be powered by a power source, which may comprise a current source and/or a voltage source for providing the power for the signal delivered to the cardiac-related sympathetic nerve in the extracardiac intrathoracic neural circuit by the at least one transducer. The power source may also provide power for the other components of the device, such as the microprocessor, memory and communication subsystem (described below). The power source may comprise a battery and may be rechargeable. It will be appreciated that the availability of power is limited in implantable devices, and the invention has been devised with this constraint in mind. The device/system may be powered by inductive powering or a rechargeable power source.

The implantable device may comprise a communication subsystem, for instance comprising a transceiver coupled to the processor. The transceiver may use any suitable signaling process such as RF, wireless, infrared and so on, for transmitting signals outside of the body, for instance to a system of which the implantable device is one part.

System Including Implantable Device

The implantable device of the invention may be part of a system that includes a number of subsystems. For instance, the system may comprise subsystems located outside of the body, including a subsystem for wirelessly recharging the battery used to power the implantable device, and a controller with a communications subsystem that is configured to communicate with the communications subsystem of the implantable device.

The controller may comprise an actuator which, upon being pressed by a physician or the subject for instance, will deliver a signal, via the respective communications subsystems, to trigger the processor of the implantable device to deliver a signal to the cardiac-related sympathetic nerve in the extracardiac intrathoracic neural circuit by the at least one transducer. Suitable signals for use with the invention are discussed above.

The controller may also be configured to make adjustments to the operation of the implantable device. For instance, it may transmit, via the respective communications subsystems, physiological data pertaining to a normal heart rhythm. The data may be specific to the patient into which the device is implanted. The controller may also be configured to make adjustments to the operation of the power source, signal generation and processing elements and/or electrodes in order to tune the signal current delivered to the cardiac-related sympathetic nerve in the extracardiac intrathoracic neural circuit by each node of the electrode.

A device/system of the invention is preferably made from, or coated with, a biostable and biocompatible material. This means that the device/system is both protected from damage due to exposure to the body's tissues and also minimizes the risk that the device/system elicits an unfavourable reaction by the host (which could ultimately lead to rejection). The material used to make or coat the device/system should ideally resist the formation of biofilms. Suitable materials include, but are not limited to, poly(p-xylylene) polymers (known as Parylenes) and polytetrafluoroethylene.

A device/system of the invention will generally weigh less than 50 g.

General

The term "comprising" encompasses "including" as well as "consisting" e.g. a composition "comprising" X may consist exclusively of X or may include something additional e.g. X+Y. The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless otherwise indicated each embodiment as described herein may be combined with another embodiment as described herein.

BRIEF DESCRIPTION OF THE DRAWINGS

FIGS. 2A-7C demonstrate the application of the invention using kilohertz frequency alternating current (KHFAC). FIGS. 8A-15B demonstrate the application of the invention using direct current (DC).

FIG. 2A is a schematic diagram showing the experimental set up for the results shown in the FIGS. 2A-5B. KHFAC was delivered to the ansae subclavia in dogs (inset for FIG. 2A). Electrical stimulation (RSS) was applied to the stellate ganglion upstream of the ansae subclavia to activate sympathetic efferent projections to the heart.

FIGS. 6B and 6D), respectively, in response to the left-sided (LT3; FIGS. 6C and 6D) and right-sided stellate T3 (RT3; FIGS. 6A and 6B) paravertebral chain ganglion stimulation before, during and after KHFAC delivery to the T1-T2 paravertebral chain ganglion. *p<0.05 from control.

FIGS. 7A-7C show the percentage change in heart rate (FIG. 7A), percentage change in contractility (LV+dp/dt; FIG. 7B) and percentage change in activation-recovery interval (ARI; FIG. 7C) at KHFAC onset when delivered at varying frequencies (5 kHz to 20 kHz) and voltages (5 to 20 V).

FIGS. 8A-12D demonstrate the application of the invention using direct current (DC).

FIGS. 8A and 8B shows the evoked cardiac responses when direct current (DC; A: 4-10-2, 6 mA/0.6 mA; B: 4-7-2, 6 mA/0.6 mA) was delivered to the ansae subclavia in a reactive (FIG. 8A) and a pre-emptive (FIG. 8B) manner. Panels from the bottom show the following parameters over time: heart rate (beats/min); left ventricular pressure (LVP; mmHg); left ventricular contractility (LV dp/dt; mmHg/s); right stellate ganglion stimulation (Grass); DC delivery.

FIG. 11 shows the evoked cardiac response to the T2 paravertebral chain ganglion stimulation before, during and after DC delivery to the T1-T2 paravertebral chain ganglion. Panels show the following parameters over time: (from bottom) left ventricular pressure (LVP; mmHg); left ventricular contractility (LV dp/dt; mmHg/s); heart rate (beats/min); DC delivery (2.5 mA, 2-4-2 1 cycle); RSS stimulation of the right T2 ganglion.

FIGS. 12B-12D shows the percentages change T2 evoked changes in heart rate (FIG. 12B), left ventricular contractility (LV dP/dt+; FIG. 12C) and ventricular activation-recovery interval (ARI; FIG. 12D) at different amplitudes of DC current, all delivered as CBDCC. Negative values indicate suppression of T2 evoked response. Data for various animals are shown: DC6 (•), DC8 (o), DC10 (▼), DC11 (Δ), DC12 (■), DC13 (□), DC14 (♦).

FIG. 13 shows the MRI image of a porcine heart at 6 weeks following induced MI.

FIG. 15B shows the effects of CBDCC on S2 effective refractory period in the chronic MI model pigs. P<0.05 vs baseline.

MODES FOR CARRYING OUT THE INVENTION

Study 1-KHFAC

Figure 1:
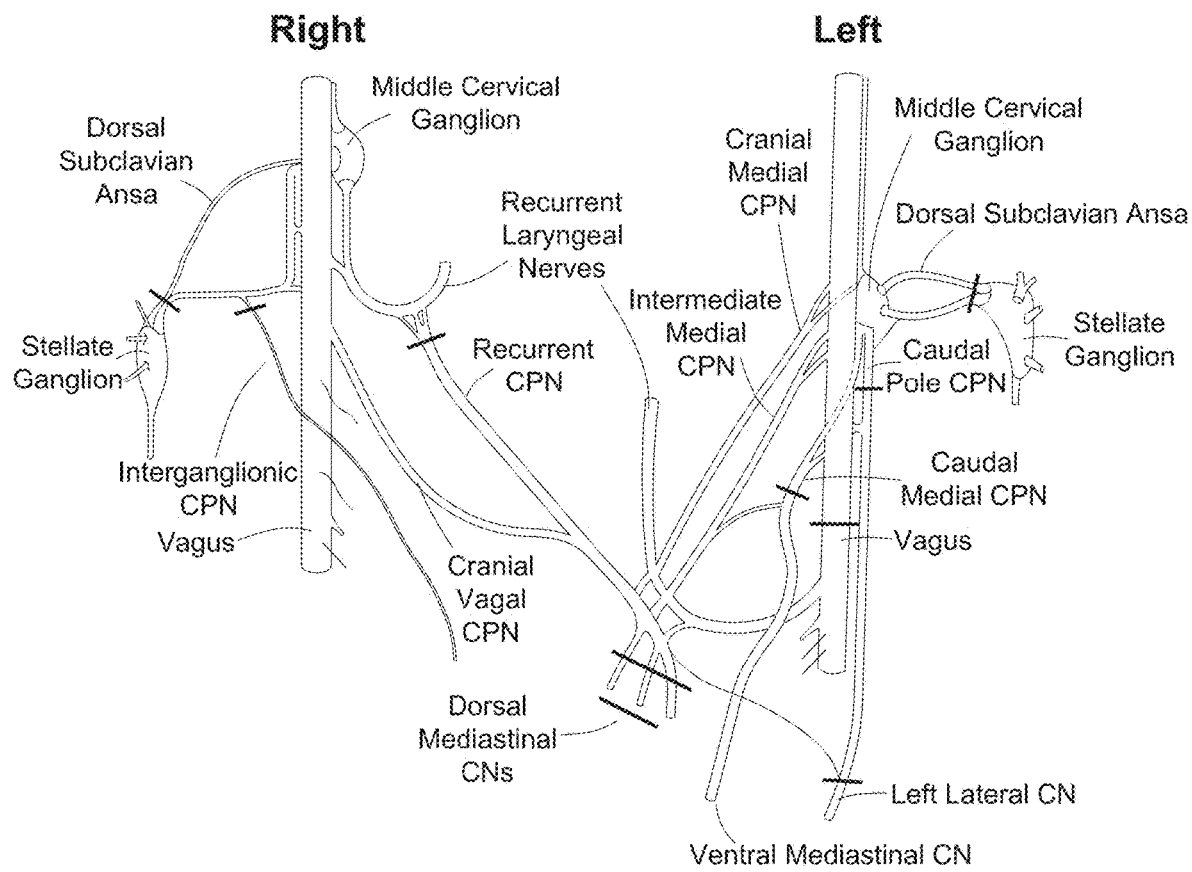
FIG. 1 is a schematic diagram depicting the gross anatomic arrangement of the upper thoracic paravertebral chain (T1-T4) and associated mediastinal neural structures, including stellate and middle cervical (MCG) ganglia.
Figure 2A:
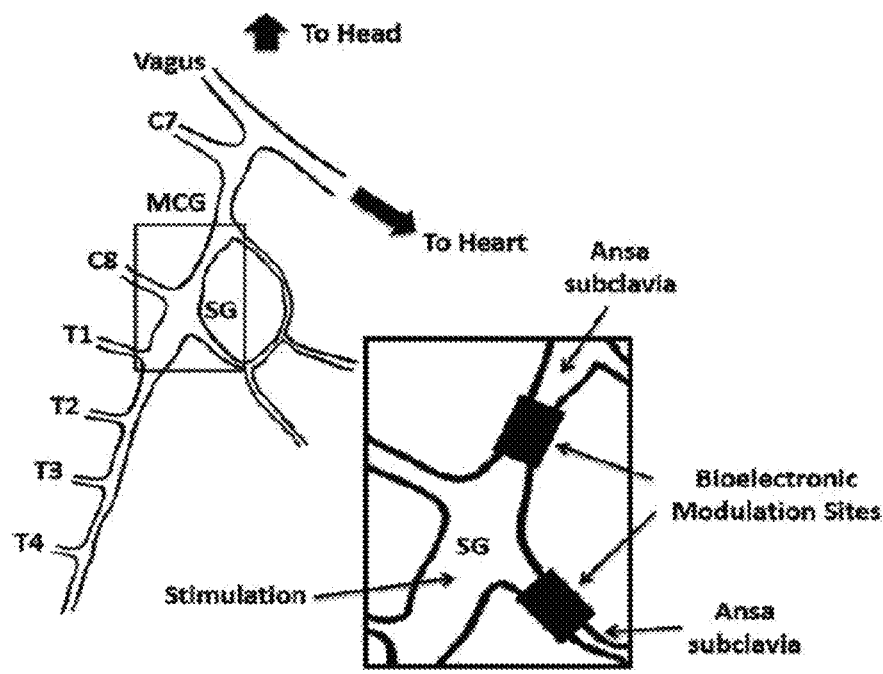

This study investigated the evoked cardiac responses to the delivery of KHFAC at a nodal intervention point in dogs. The communication between stellate and middle cervical ganglia, namely the ansae subclavia, was targeted for neural block, and the experimental set up is shown in FIG. 2A. Stellate ganglion simulation (RSS) was delivered by Grass S88 Stimulator at 4 Hz. KHFAC was delivery to the ansae subclavia by a voltage controlled block (Stanford Research Systems DS 345 waveform generator). Cardiac readouts, indicative of functional sympathetic inputs to the heart, included heart rate (beats/min), ventricular contractility (+dP/dt), and ventricular pressure (LVP) were recorded.

The results are shown in FIGS. 2-5b. KHFAC delivery to the ansae subclavia successfully evoked changes in regional cardiac function.

Figure 2B:
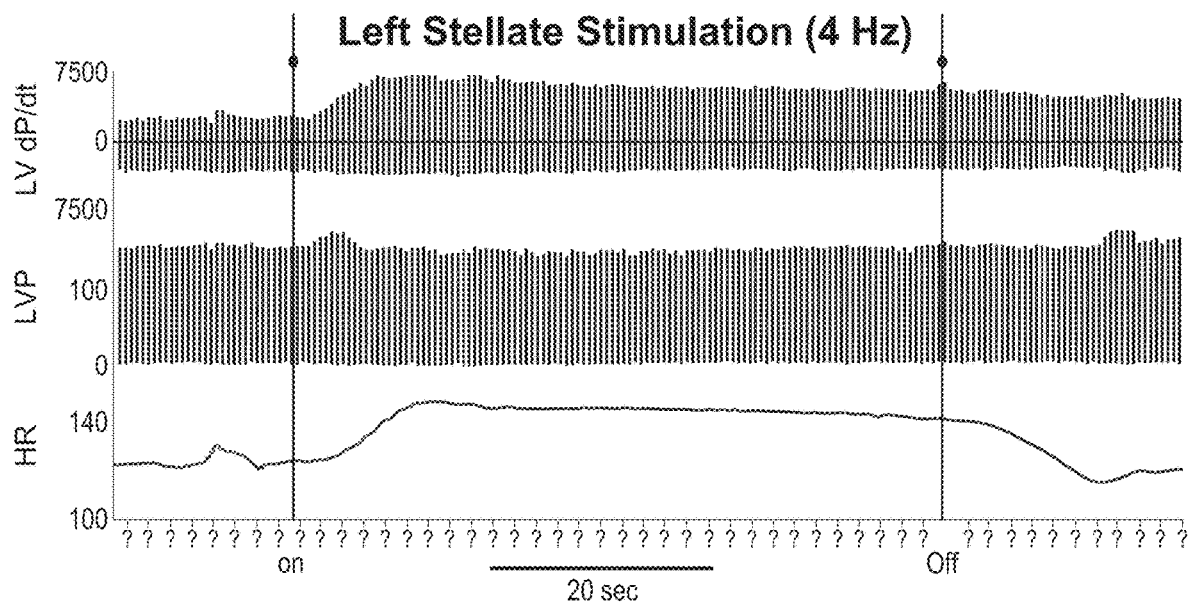
FIG. 2B shows the evoked cardiac responses to the stimulation of the left stellate ganglion (4 Hz; depicted by "ON" and "OFF"). Panels showing the following parameters over time (from bottom): heart rate (beats/min), left ventricular pressure (LVP; mmHg) and left ventricular contractility (as reflected in the changes in LV dP/dt; mmHg/s).
Figure 2C:
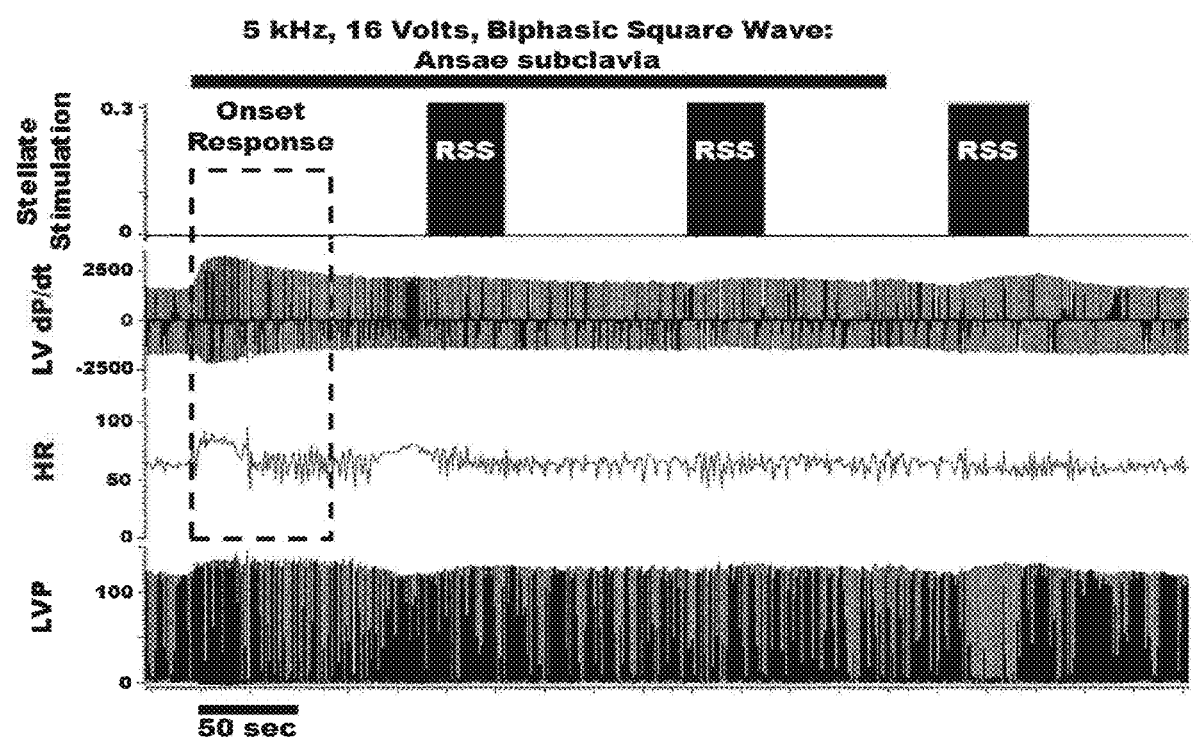
FIG. 2C shows the evoked cardiac responses to KHFAC and RSS delivery. Panels show the following parameters over time (from bottom): left ventricular pressure (LVP; mmHg); heart rate (beats/min); left ventricular contractility (LV dP/dt; mmHg/s); stellate cardiac ganglion stimulation (RSS), KHFAC delivery at 5 kHz, 16 V, biphasic square wave). Box: onset response to KHFAC.

The stimulation of the stellate ganglion (RSS) led to an increase in cardiac contractility and heart rate (FIG. 2B). The increase in contractility and heart rate was reduced by KHFAC delivery (5 kHz, 16 V, biphasic square wave) to the ansae subclavia (FIG. 2C). During KHFAC delivery, the cardiac responses to sympathetic efferent activation were blunted.

The sympathetic neurons also demonstrated a delayed recovery (FIGS. 2C and 4) showing that a small duration of KHFAC delivery could induce prolonged block of up to 30 minutes.

Figure 3A:
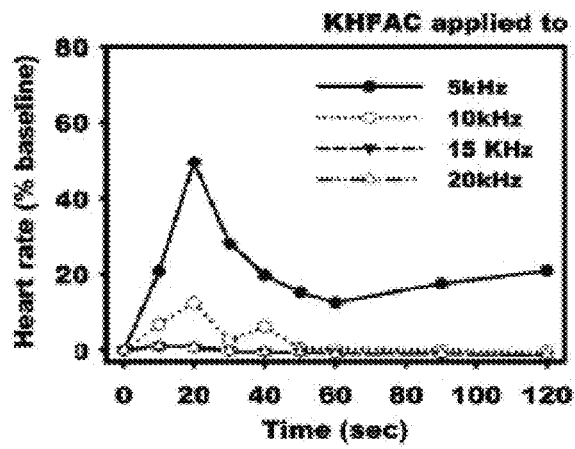
FIG. 3A shows the percentage change in the heart rate over the initial 120 seconds after onset of KHFAC delivery at different frequencies: 5 kHz (Δ), 10 kHz (▼), 15 kHz (o) and 20 kHz (•).
Figure 3B:
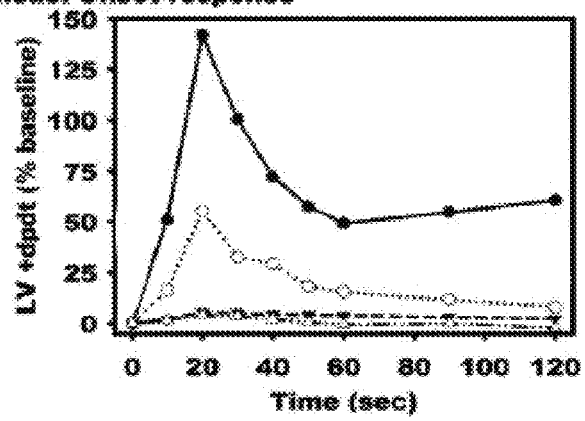
FIG. 3B shows the percentage change in the left ventricular contractility (LV+dP/dt) over the initial 120 seconds after onset of KHFAC delivery at different frequencies: 5 kHz (Δ), 10 kHz (▼), 15 kHz (o) and 20 kHz (•).
Figure 3C:
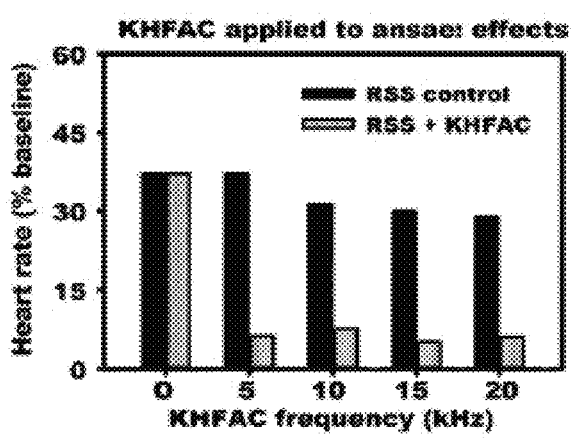
FIG. 3C shows the percentage change in heart rate in response to RSS before (black bars) and during KHFAC delivery. KHFAC delivered at frequencies of 5 kHz, 10 kHz, 15 kHz and 20 kHz.
Figure 3D:
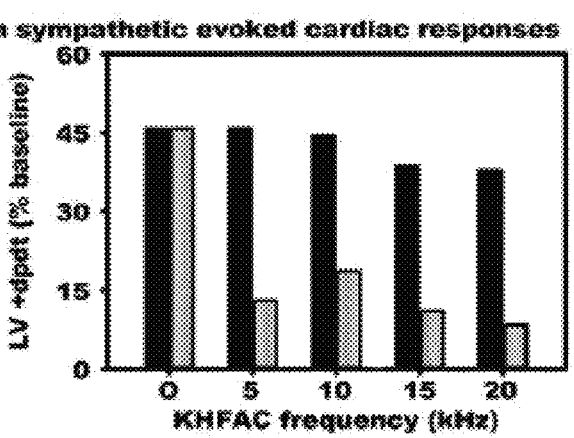
FIG. 3D shows the percentage change in LV+dp/dt in response to RSS before (black bars) and during KHFAC delivery. KHFAC delivered at frequencies of 5 kHz, 10 kHz, 15 kHz and 20 kHz.
Figure 4A:
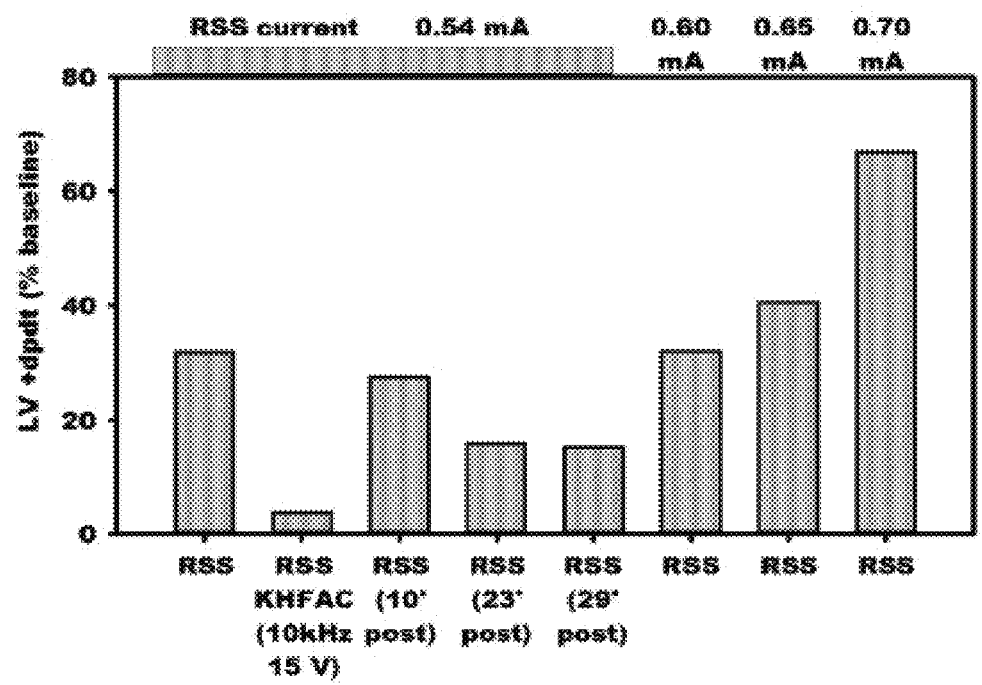
FIGS. 4A and 4B show effects of KHFAC delivered to the ansae on the RSS evoked changes in LV+dp/dt (FIG. 4A) and heart rate (FIG. 4B). Bars from left to right: before KHFAC delivery (RSS at 0.54 mA); RSS delivered during KHFAC (10 kHz, 15V); RSS delivered 10', 23' and 29' after KHFAC termination. Last three bars indicate cardiac responses to increasing RSS stimulus intensity to 0.6 mA, 0.65 mA and 0.7 mA.
Figure 4B:
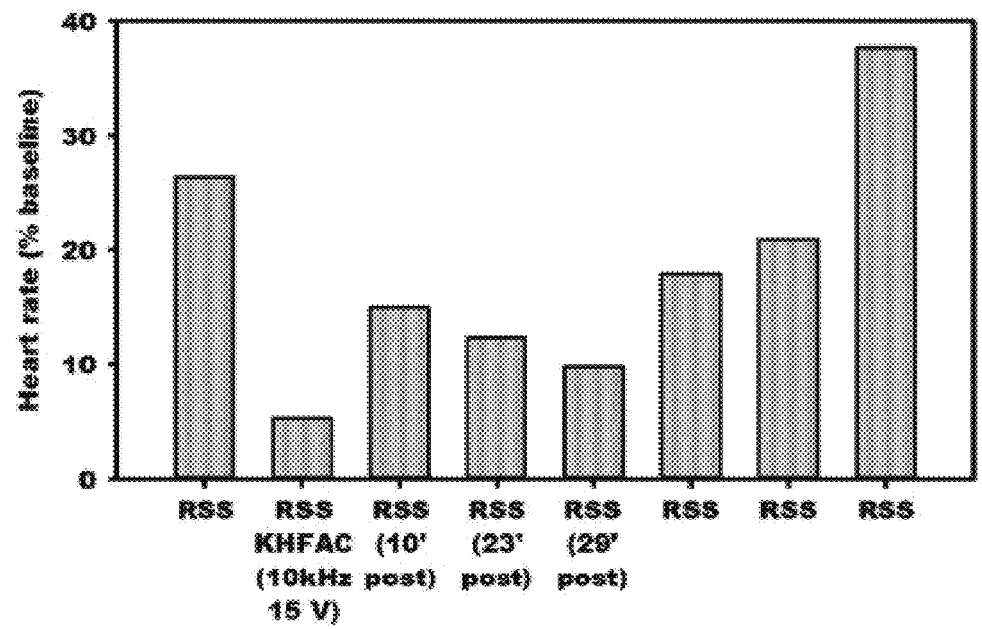

A clear dose response was also identified in FIGS. 3 and 4 with blocking levels related to frequency and intensity among other factors.

KHFAC evoked a transient sympatho-excitation at onset that was voltage-dependent and inversely related to frequency (see FIGS. 2C, 3A and 3B), but was nonetheless efficacious in reducing sympathetic activation after the initial onset phase (FIGS. 3C, 3D and 4).

Thus, this study demonstrates that sympathetic signals to the heart could be blocked by applying electrical signals, e.g. KHFAC, to the ansae subclavia.

Study 2-KHFAC

This study investigated the reversibility of cardiac responses to KHFAC delivery to either the ansae subclavia or the T1-T2 paravertebral chain ganglion in pigs.

Figure 5A:
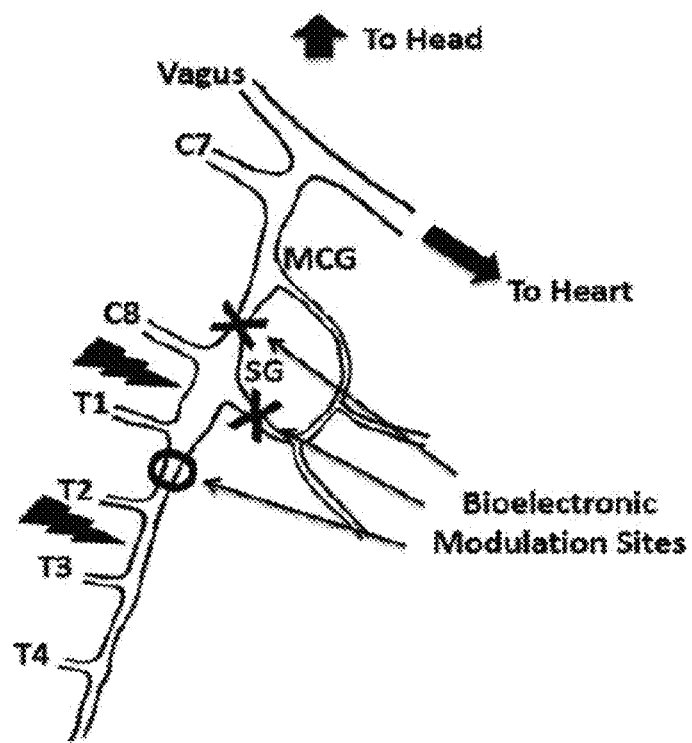
FIG. 5A is a schematic diagram showing the experimental set up for the results shown in FIGS. 5A-7C for evaluation of KHFAC. The schematic diagram depicts the gross anatomic arrangement of the porcine right-sided upper thoracic paravertebral chain (T1-T4) and the lower cervical paravertebral chain. SG=stellate ganglion. MCG=middle cervical ganglion. CPN=cardiopulmonary nerves. "X" depicts KHFAC delivery sites at the ansae sublavia and the "open circle" depicts KHFAC delivery sites at the T1-T2 paravertebral chain. Lightning bolts indicate RSS stimulation sites at the T3 paravertebral chain and at the C8-T1 paravertebral chain.

The experimental set up is outlined in FIG. 5A. KHFAC (15 kHz, 15 Volts, biphasic square wave) was delivered at either the T1-T2 paravertebral chain ganglion or ansae subclavia. Electrical simulation to activate sympathetic efferents was delivered at either the T3 paravertebral chain or the C8-T1 paravertebral chain (location of stellate ganglion).

KHFAC Delivery to Ansae Subclavia

Figure 5B:
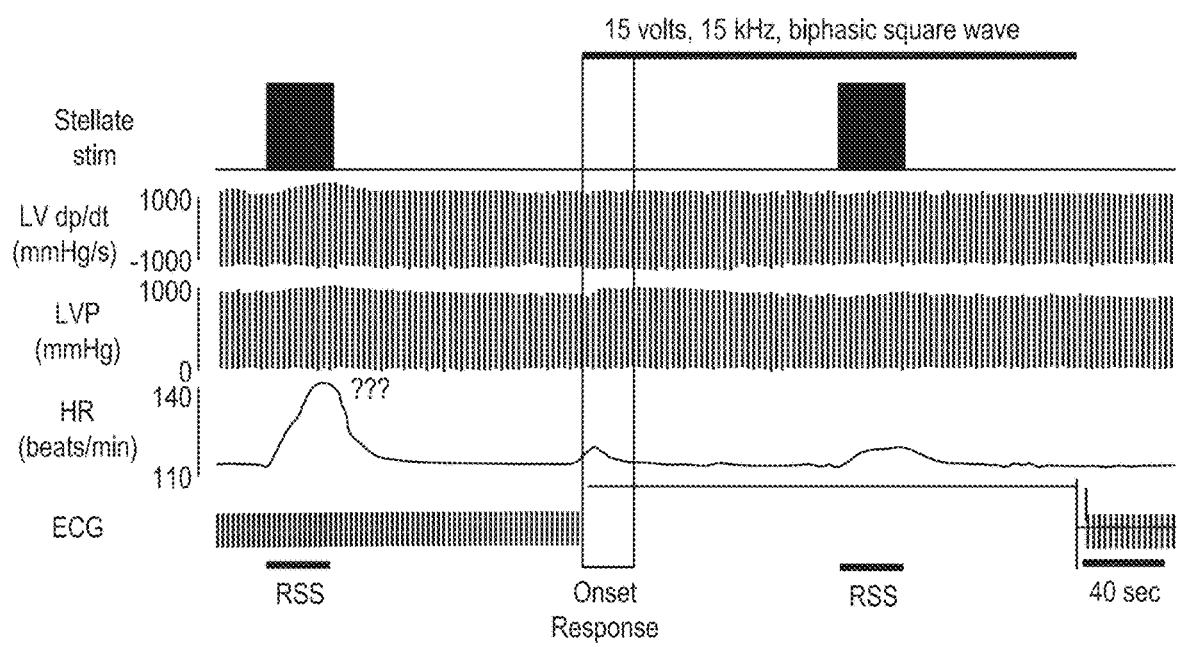
FIG. 5B shows the evoked cardiac responses to KHFAC delivery to the ansae subclavia and RSS delivery at the T3 ganglion prior to and during KHFAC. Panels show the following parameters over time: (from bottom) electrocardiac diagram (ECG); heart rate (beats/min); left ventricular pressure (LVP; mmHg); left ventricular contractility (LV dP/dt; mmHg/s); stellate stimulation (RSS); KHFAC delivery (15 kHz, 15 Volts, biphasic square wave) to the ansae subclavia. Boxed: onset response.
Figure 6A:
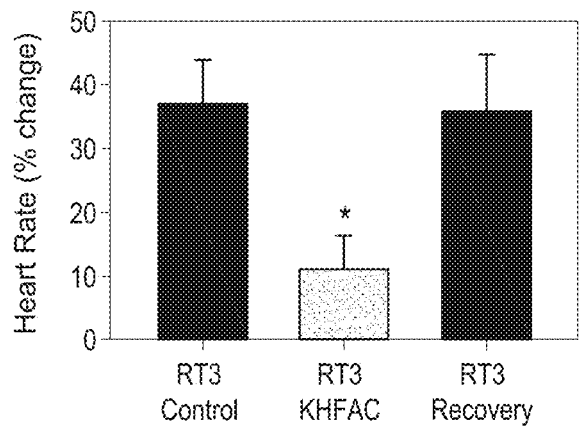
FIGS. 6A-6D show the percentage change in heart rate (FIGS. 6A and 6C) and the percentage change in left ventricular contractility (LV+dp/dt.
Figure 6B:
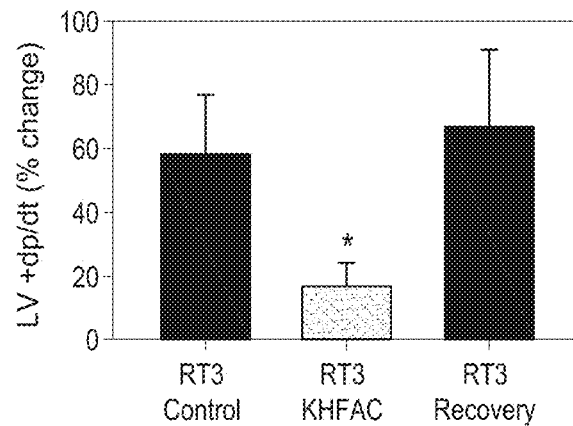
Figure 6C:
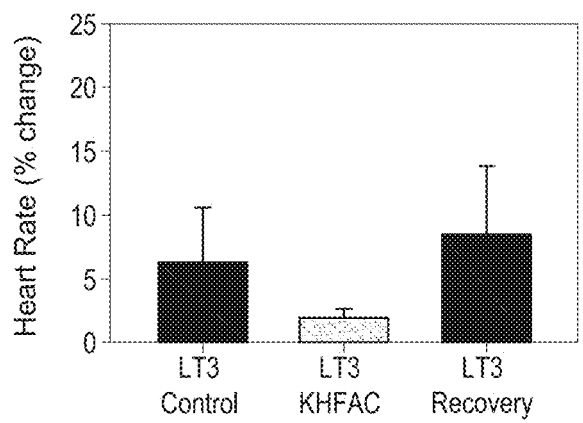
Figure 6D:
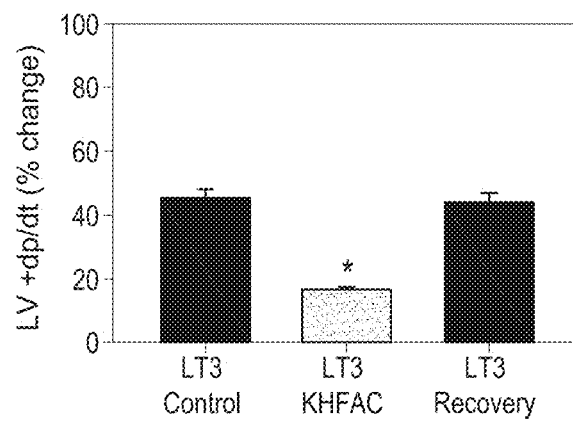

The effects of KHFAC delivery to the ansae subclavia are shown in FIG. 5B. Referring to FIG. 5B, stellate stimulation led to an increase in cardiac function (increase in heart rate, increase in left ventricular pressure and increase in left ventricular contractility). This increase was reduced by KHFAC delivery to the ansae subclavia. During KHFAC delivery, further stellate stimulation resulted in minimum cardiac responses.

KHFAC Delivery to T1-T2 Paravertebral Chain Ganglion

The effects of KHFAC delivery to the T1-T2 paravertebral chain ganglion are shown in FIG. 6. It can be seen that chronotropic (FIGS. 6A and 6C) and inotropic (FIGS. 6B and 6D) functions in response to T3 stimulation was significantly reduced during KHFAC delivery, and the reductions in evoked responses reversed after KHFAC delivery.

Onset Response

Figure 7A:
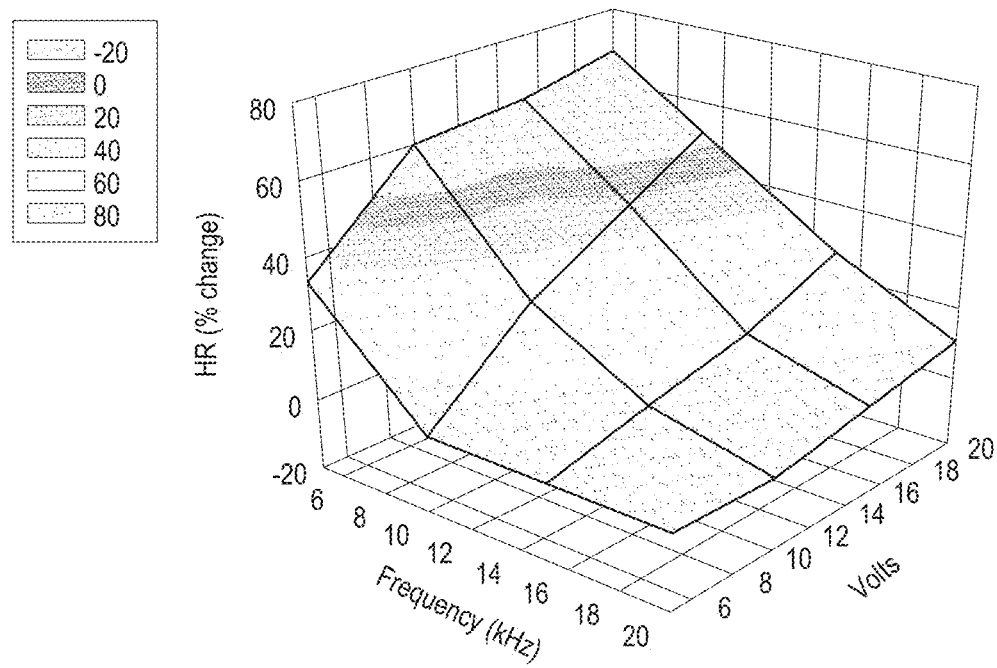
Figure 7B:
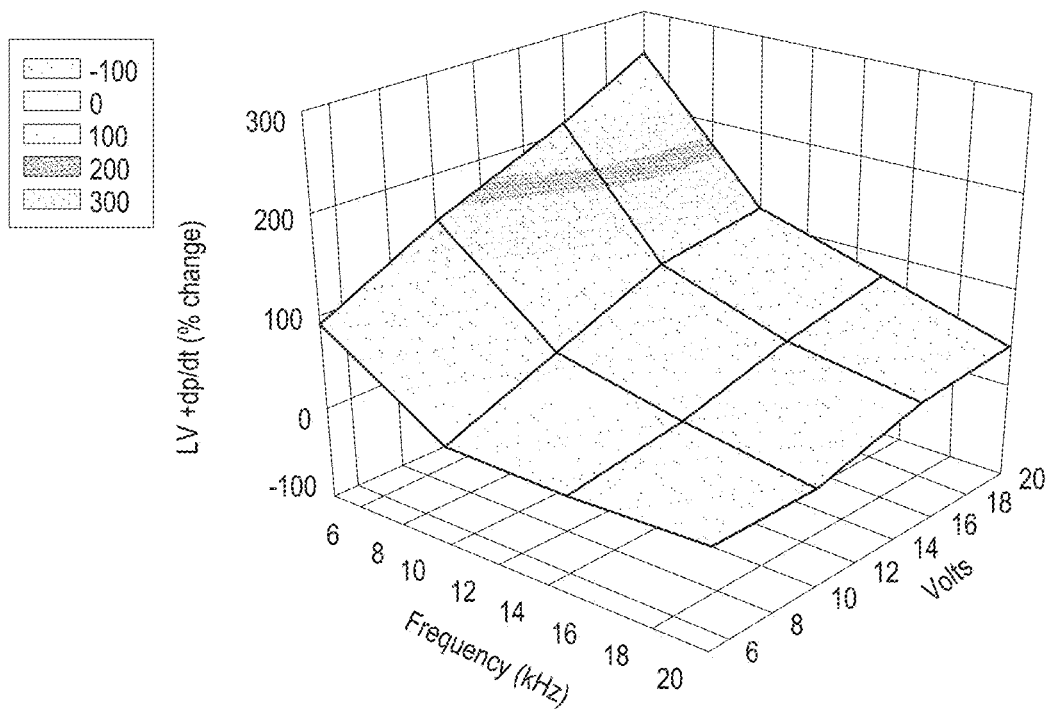
Figure 7C:
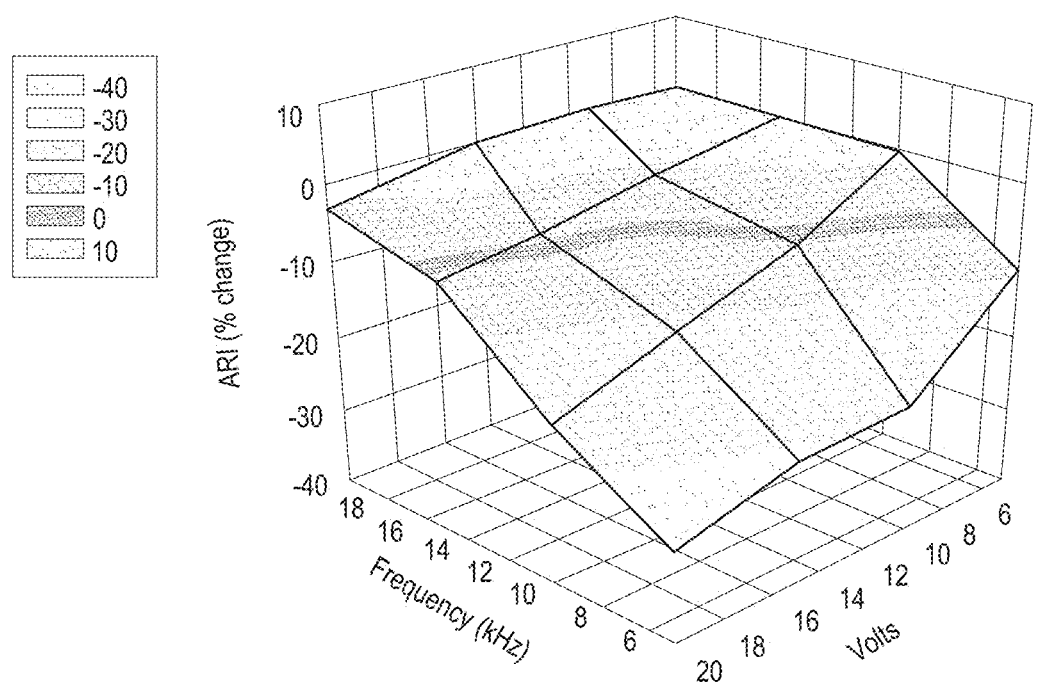

The onset response following KHFAC was further investigated. In particular, the chronotropic, inotropic and dromotropic responses were measured with KHFAC delivery at varying frequencies and voltages, and the results are shown in FIG. 7.

It was considered that KHFAC onset response reflects transient activation of underlying nerve tracts prior to block induction. It seems that, for the onset response, lower frequency ranges with higher intensities generate bigger onset responses. The onset response may be minimized by modifying parameters and studying the effect, for example by (1) lowering the frequency, lowering intensity and changing the waveform, or (2) ramp titration starting from high frequency-low intensity to target levels. For example, Ackermann et al. demonstrated that onset response may be completely neutralized by using a brief DC nerve block prior to application of the KHFAC signal. The use of KHFAC in combination with a DC nerve block is also contemplated for the present invention.

Thus, this study demonstrates the reversibility of the block of the sympathetic signals to the heart by applying electrical signals, e.g. KHFAC, to either the ansae subclavia or the T1-T2 paravertebral chain ganglion.

Study 3—DC

This study investigates the evoked cardiac responses to DC delivery at a nodal intervention point. This study is set up in a similar way as the previous studies, except DC was delivered to the ansae subclavia. This study was done in both canine and porcine models.

The results are shown in FIG. 8. These experiments were done in the anesthetized canine model. It can be seen that DC block was effective in a reactive and pre-emptive manner. In particular, FIG. 8A shows that DC block was effective when used in a reactive manner. When DC was delivered during right stellate stimulation (RSS), the increase in the chronotropic and inotropic functions in response to RSS stimulation was reduced during the period of DC delivery.

Figure 8A:
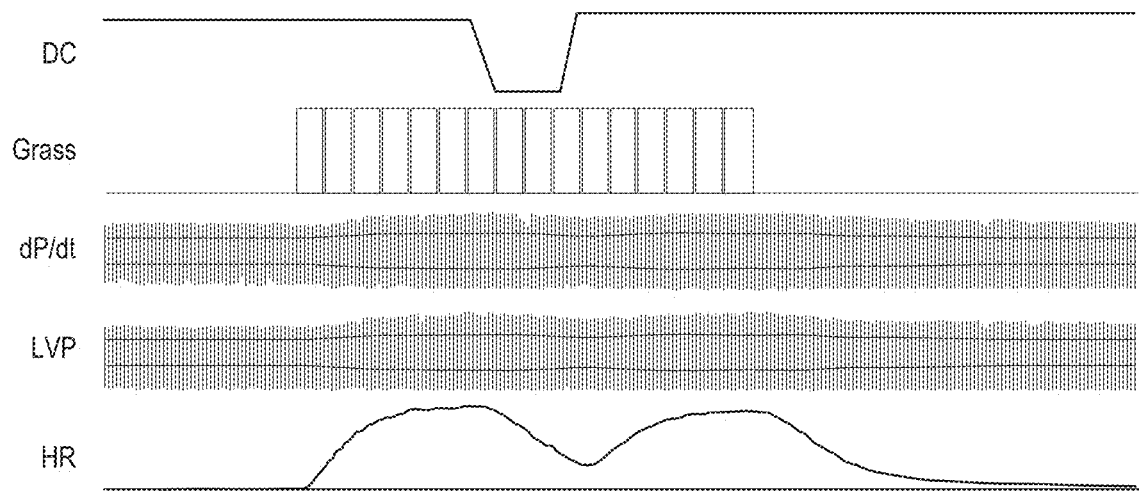
Figure 8B:
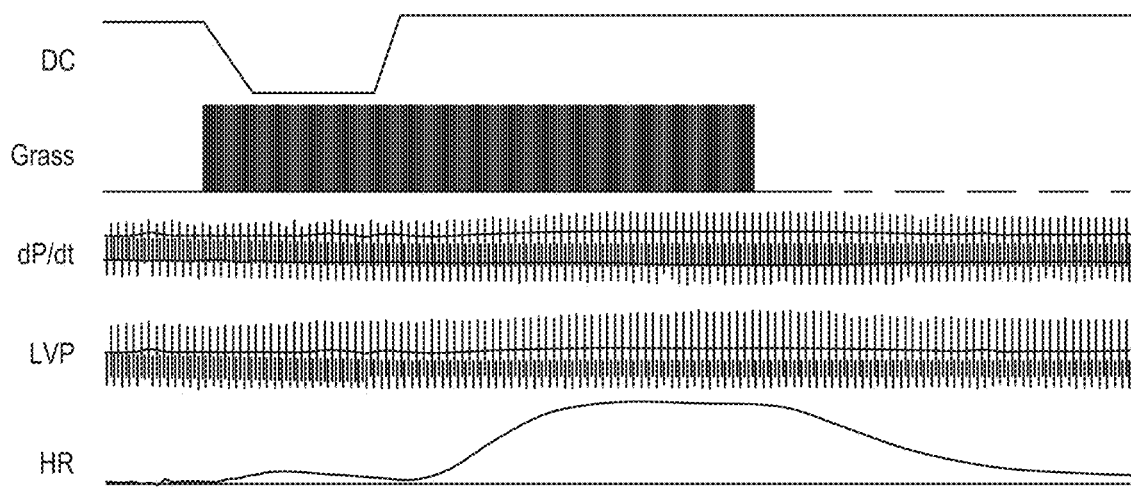
Figure 8C:
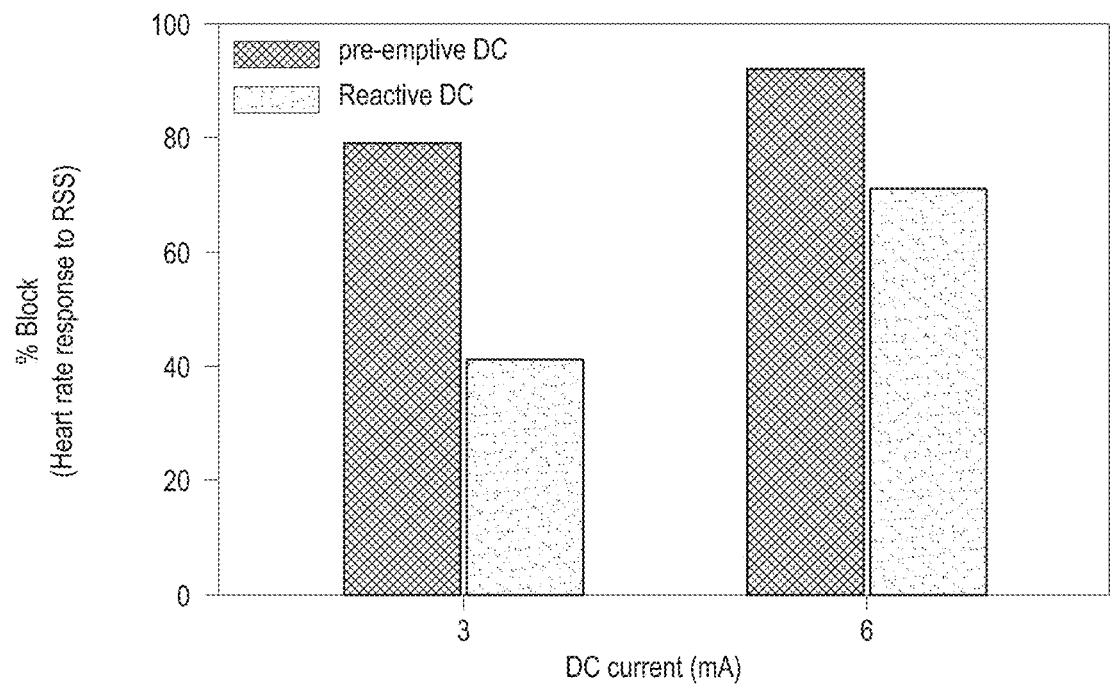
FIGS. 8C and 8D show the percentage of block of heart rate and contractility (dP/dt+), respectively, when DC was delivered at 3.0 mA and 6.0 mA. Black bars=pre-emptive. gray bars=reactive.
Figure 8D:
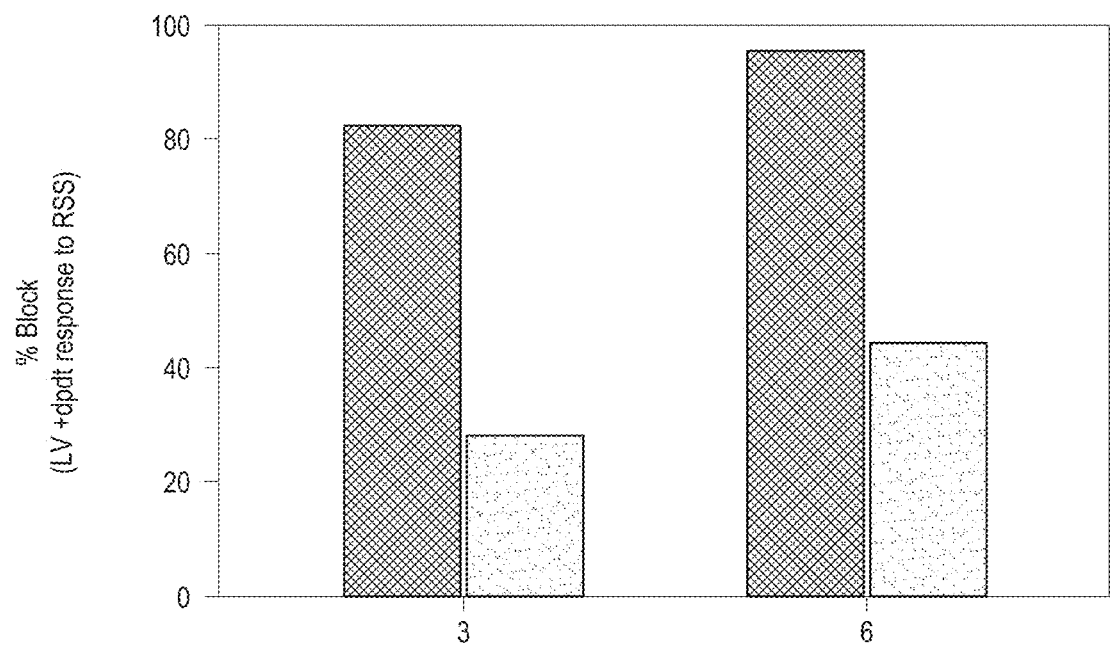

FIG. 8B shows that DC block was effective when used in a pre-emptive manner. When DC was delivered at the onset of RSS stimulation, the increase in the chronotropic and inotropic functions in response to RSS stimulation was not achieved until after DC delivery was removed.

Interestingly, the percentages block of chronotropic (FIG. 8C) and inotropic (FIG. 8D) responses were highly effective for DC pre-emptive use, with 80% block at 3 mA, and increasing to nearly 100% at 6 mA, for both inotropic and chronotropic responses.

Thus, this study has established for the first time that neural block of cardiac sympathetic regulation at a nodal intervention was effective for reactive, and particularly effective for pre-emptive, treatments of ventricular arrhythmias.

Study 4—DC

This study investigated the cardiac responses to DC delivery with increasing voltages. These experiments were done in the anesthetized canine model. The results are shown in FIG. 9.

Figure 9A:
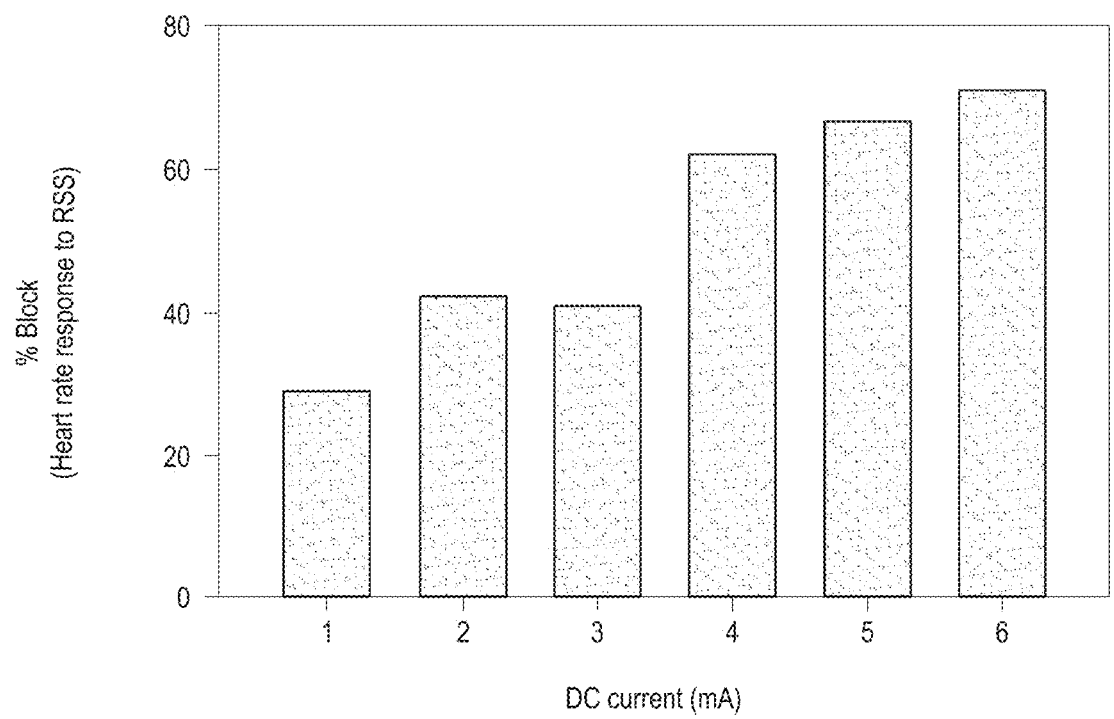
FIGS. 9A and 9B show the percentage of block of the RSS induced changes in heart rate (FIG. 9A) and LV contractility (FIG. 9B) during DC delivery to the ansae subclavia at amplitudes ranging from 0 mA to 6 mA.
Figure 9B:
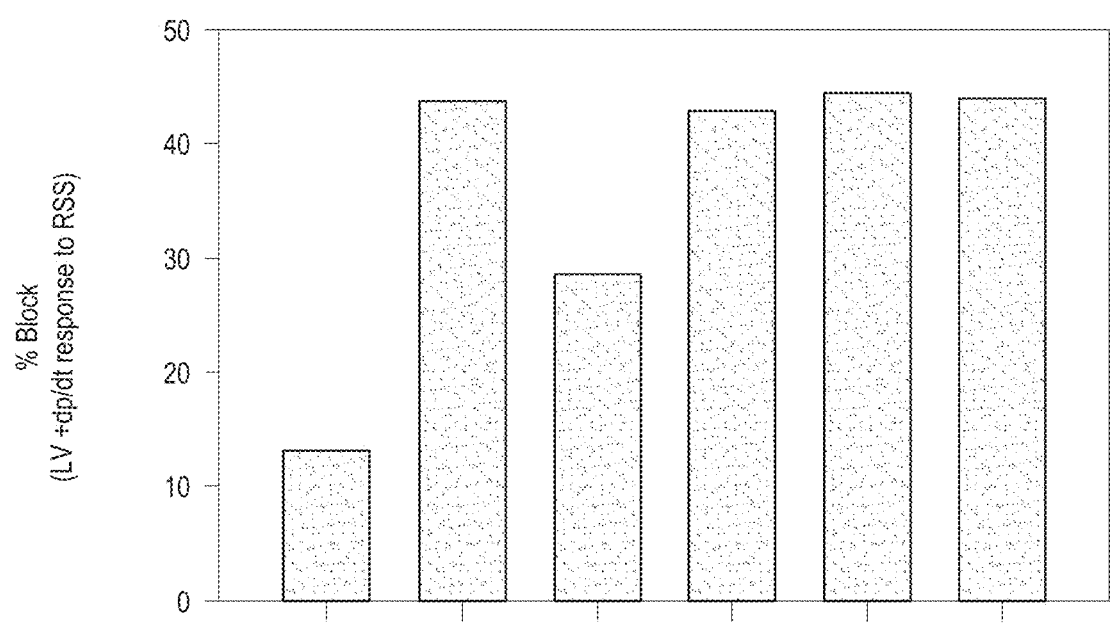

FIG. 9 shows that increasing the DC voltage/current amplitude increases the percentage block of chronotropic (FIG. 9A) and inotropic (FIG. 9B) responses.

Therefore, increasing current output was able to produce substantially greater DC block. As a corollary, the degree of block can be graded by selecting the current intensity.

Study 5—DCC

Figure 10A:
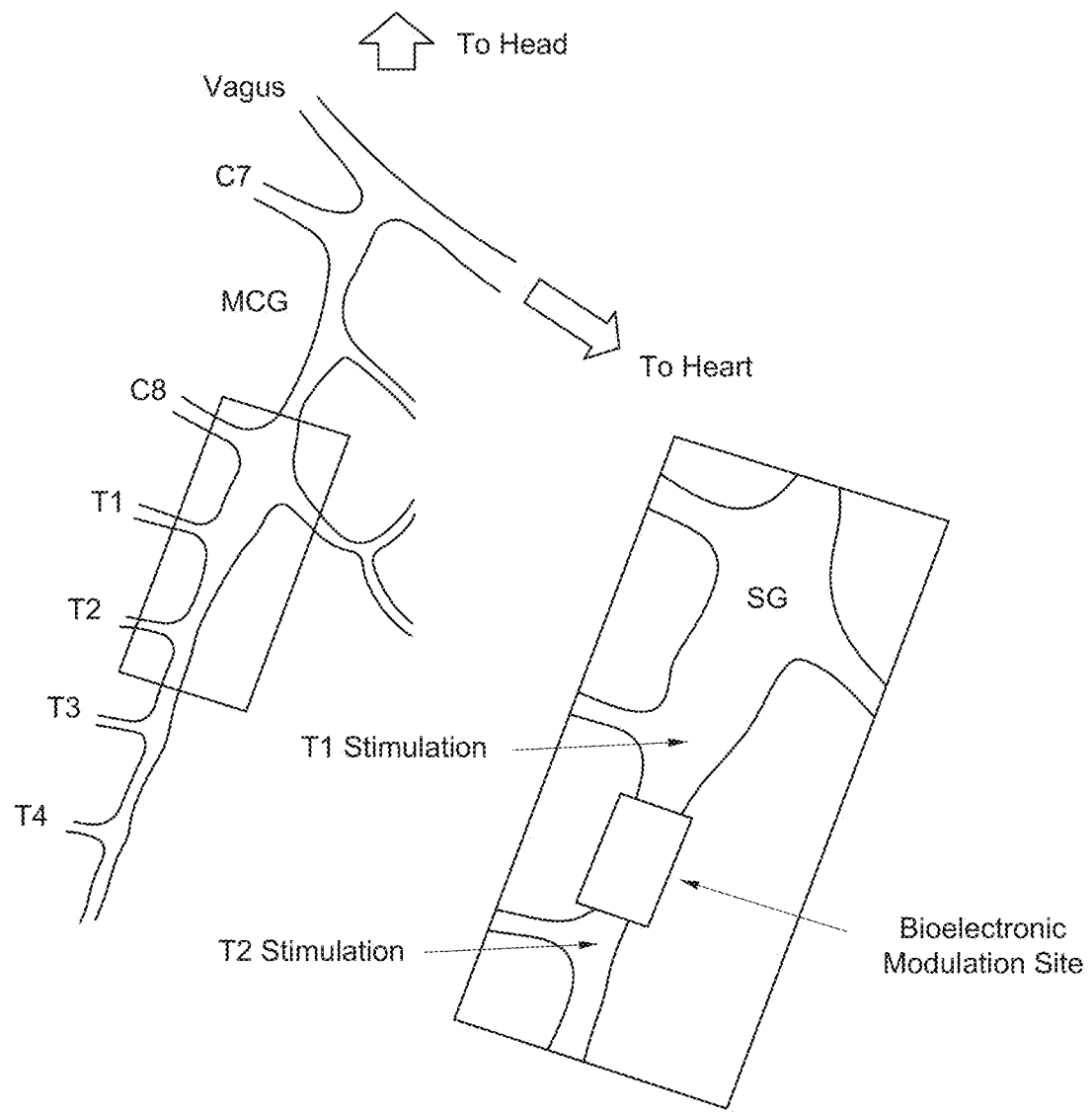
FIG. 10A is a schematic diagram showing the experimental set-up for FIGS. 11-12, 14 and 15. The schematic diagram depicts the gross anatomic arrangement of the porcine right-sided upper thoracic paravertebral chain (T2-T4) and associated mediastinal neural structures, including stellate (SG) and middle cervical (MCG) ganglia. Four DC electrodes are coupled to the region between T1-T2 paravertebral chain ganglion, and they are arranged to deliver signals one after another in cycles (DC carousel; DCC). Arrows indicate stimulation sites at the T2 paravertebral chain and at the stellate ganglion (insert for FIG. 10A).

This study investigated the cardiac responses to delivery of DC carousel (DCC). The experimental set up is shown in FIG. 10. DC was delivered to the T1-T2 paravertebral chain ganglion and ganglion stimulation was delivered at the T2 paravertebral chain and stellate ganglion (SG).

In Yorkshire pigs a median sternotomy was performed, the right thoracic paravertebral chain isolated and a 56-electrode sock placed over the ventricular epicardium. For charged balanced DC (CBDC), a 4-node CBDCC carbon black coated platinum electrode was placed under the T1-T2 segment (FIG. 10) and connected to individual DC current sources. T2 electrical stimulation with and without CBDCC, delivered at varying current intensities, was used to determine local block efficacy. Cardiac readouts, indicative of functional sympathetic inputs to the heart, included activation recovery interval (ARI), heart rate and left ventricular (L V)+dP/dt were recorded.

Figure 10B:
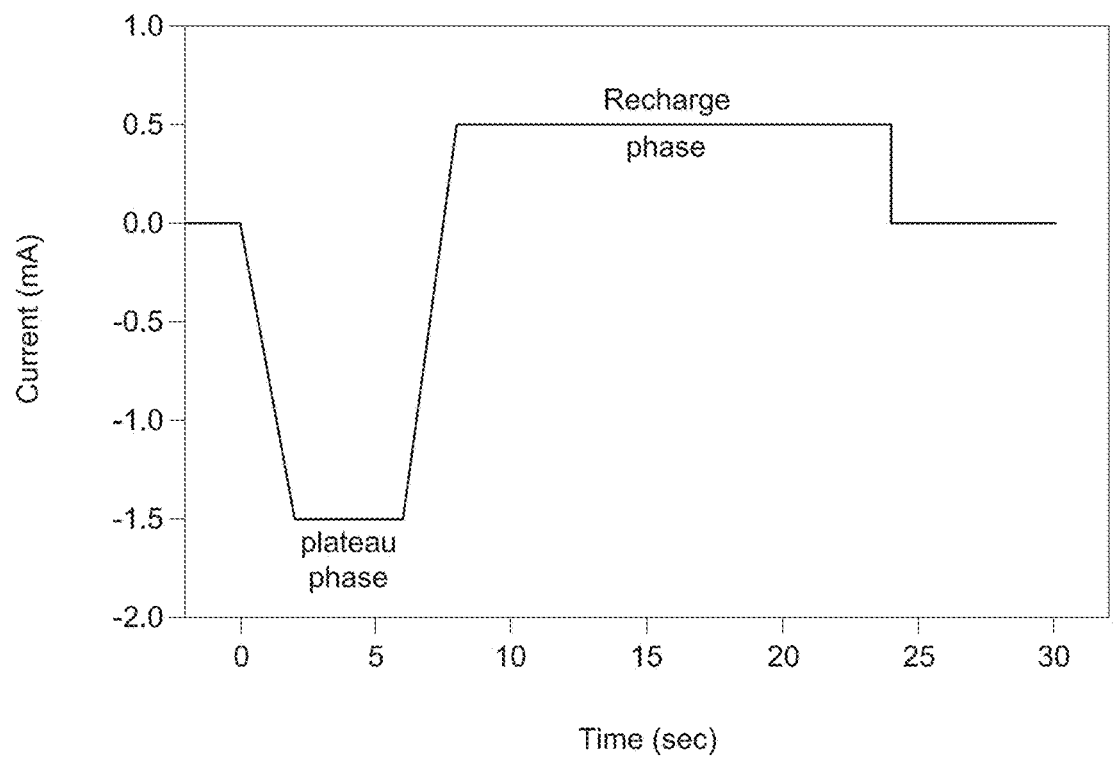
FIG. 10B shows an exemplary charged balanced biphasic DC pulse. In this iteration, there is a 2 second ramp down to a 4 second plateau, with a two second ramp up to a current in the opposite direction that is –⅓ of the plateau current and maintained for ~16 second. The critical factor is that charge delivery during the recharge phase balances that delivered during ramp and plateau phase.
Figure 10C:
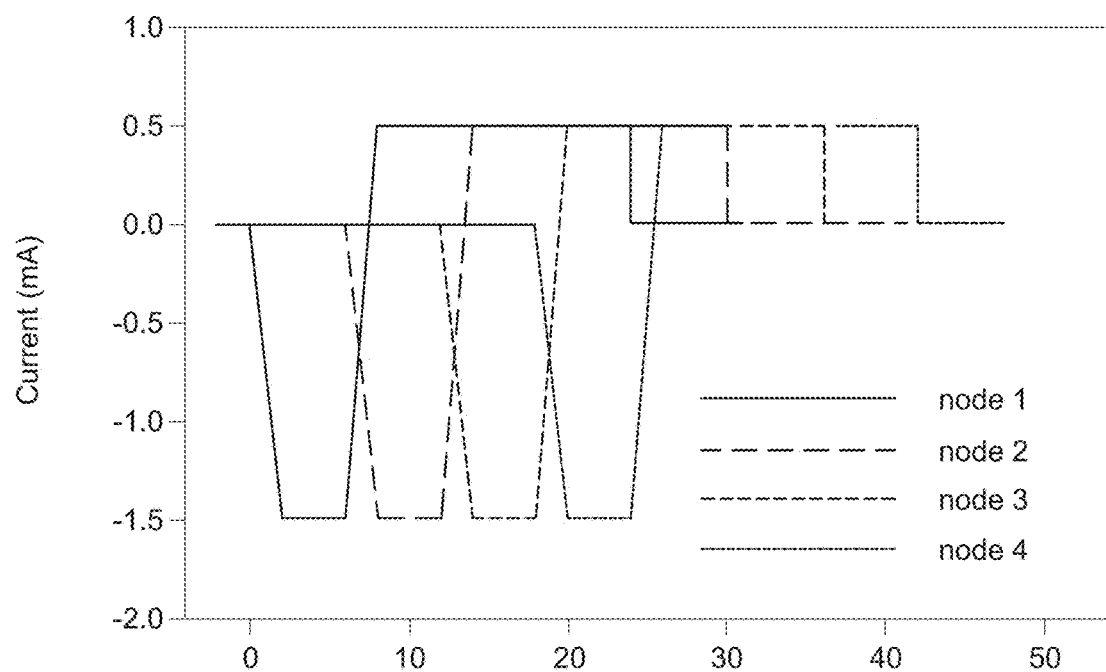
FIG. 10C shows an example of one cycle of charge balanced DC current delivery, in this case from four channel (node) electrode. In this iteration, by the time node 4 has finished its plateau phase, the first node is available for re-stimulation, thus allowing for longer-duration charge balanced DC carousel (CBDCC) bioelectric modulation.

The inventors noted that, with this design, a minimum of four nodes are required for maintained DCC block because of technical issues with charge-balance. FIGS. 10B and 10C show an illustrative waveform for a single node (FIG. 10B) or for the stimulation protocol for a 4 node CBDCC stimulation. FIG. 10C reflects a single cycle through the 4 nodes which can then be linked serially to maintain DC block.

Figure 11:
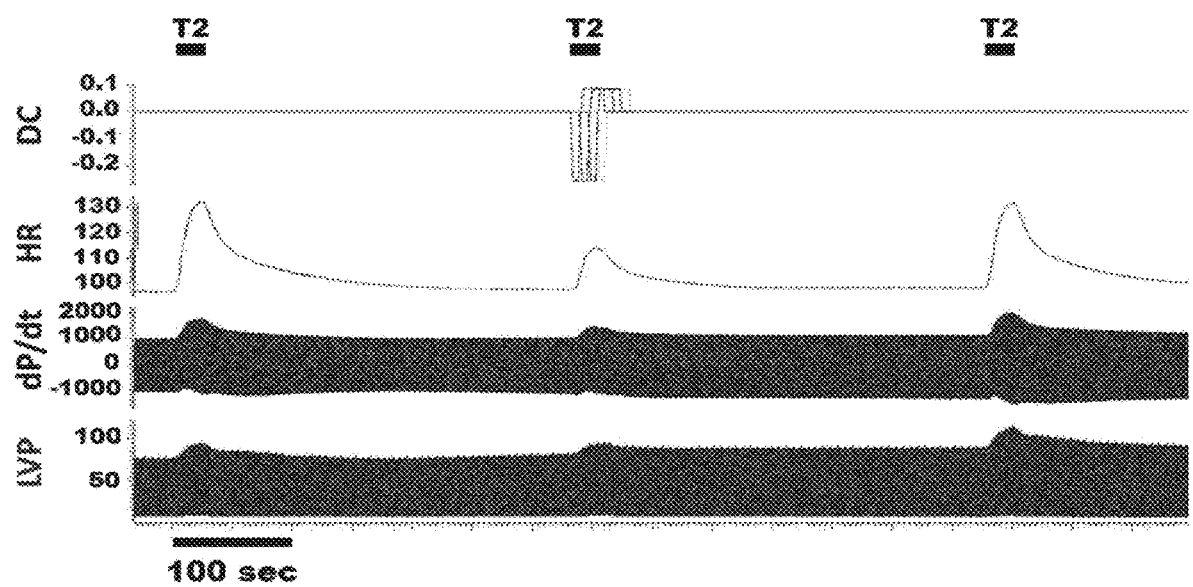

The results are shown in FIGS. 11-12. CBDCC was effective in modulating sympathetic efferent projections to the heart.

FIG. 11 shows the cardiac responses to DCC delivery to the T1-T2 ganglion. Referring to FIG. 11, stellate stimulation led to an increase in cardiac function (increase in heart rate, left ventricular pressure and left ventricular contractility). This increase was reduced by DCC delivery to the T1-T2 ganglion.

Interestingly, once DCC delivery was removed, baseline cardiac function resumed.

Figure 12A:
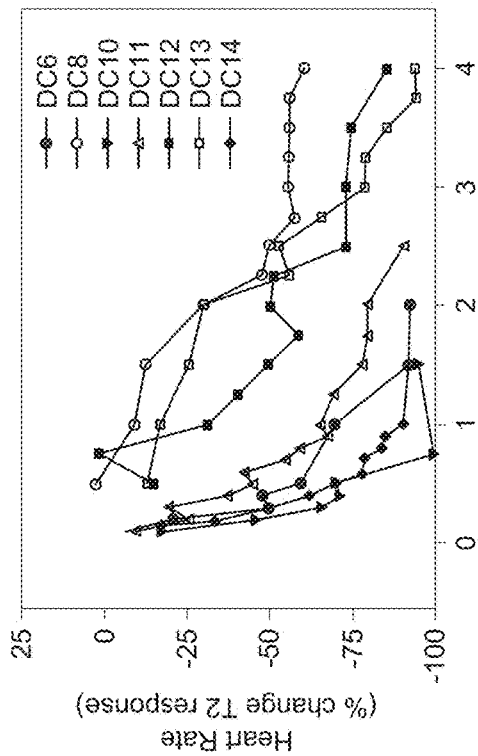
FIG. 12A shows the percentage change in heart rate, left ventricular contractility (LV dP/dt+) and activation-recovery interval (ARI) relative to the baseline in response to T2 stimulation (black bars) or in response to one cycle of charge balanced DC current (grey bars).
Figure 12B:
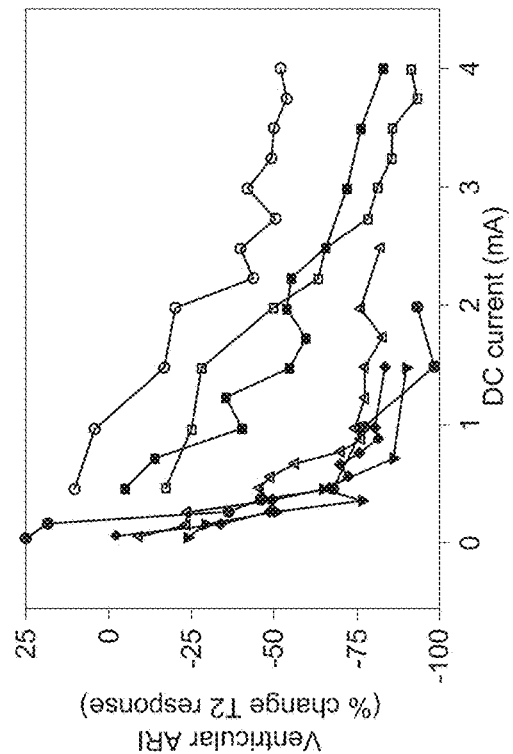
Figure 12C:
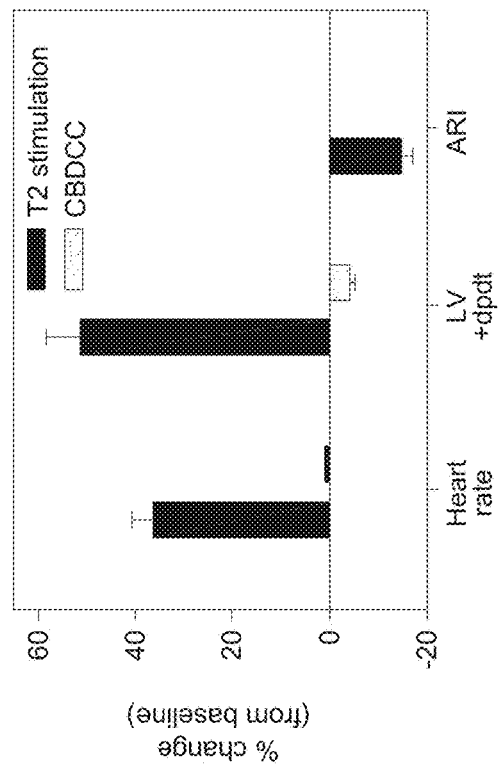
Figure 12D:
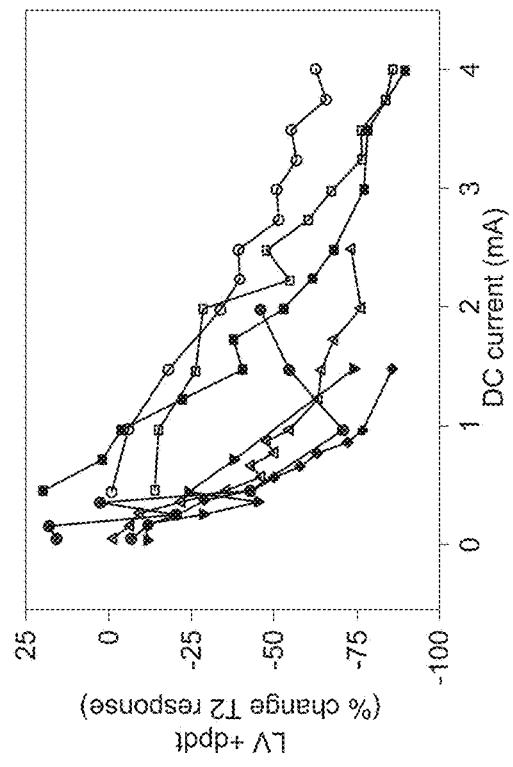

It was also found that increasing the DCC voltage/current amplitude increases the block of chronotropic (FIG. 12B), inotropic (FIG. 12C) and dromotropic (FIG. 12D) responses. Note also that CBDCC had minimal impact on basal cardiac function (FIG. 12A, grey bars).

Conclusion

This study confirmed that nodal intervention by DCC block at the upper thoracic paravertebral chain, (namely T1-T2) is highly effective in reducing the sympathetic regulation of cardiac function. Interestingly, the efficacy of a DCC block is current dependent, and because of this, each node for the DC block can be tuned to a desired degree of block by adjusting the current.

T1 stimulation proximal (upstream) to the block resulted in maintained sympathetic response.

Notably, the effects of DCC (short-term) on the nerve are reversible, so it does not alter basal cardiac function.

Study 6—DCC in Porcine Chronic MI Model

This study investigated the efficacy of charge balanced direct current (CBDC), applied to the T1-T2 region of the paravertebral chain in a carousel arrangement (CBDCC), to impact the ventricular arrhythmia potential post-myocardial infarction (MI).

Figure 13:
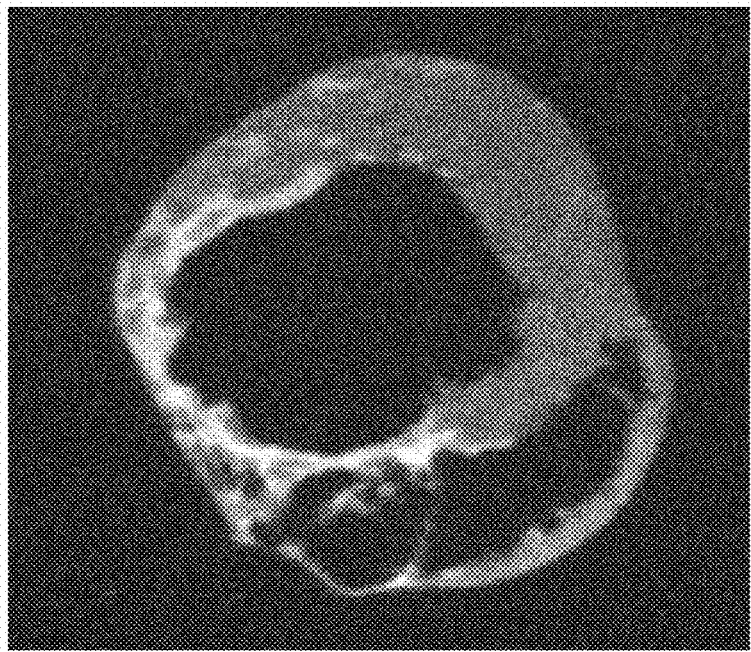

This study used a porcine chronic myocardial infarction (MI) model (n=7). In the porcine models, MI was induced beyond the first diagonal in the left anterior descending coronary artery by microsphere injection. FIG. 13 shows a representative MRI illustrating the myocardial infarct zone so created. Terminal procedures were performed (8-16 weeks) thereafter. At termination, following a mid-sternal thoracotomy, a 56-epicardial-electrode sock was placed over both ventricles and a quadripolar carousel electrode positioned underlying the right T1-T2 paravertebral chain. The efficacy of CBDC carousel (CBDCC) block was assessed by stimulating the right T3 paravertebral ganglion with and without CBDCC. Ventricular tachycardia (VT) inducibility to a S1-S2 pacing protocol was then assessed at baseline (BL) and repeated under >50% CBDCC blockade of functional sympathetic efferent projections to the heart.

The results are shown in the table below and in FIGS. 14-15.

Figure 14A:
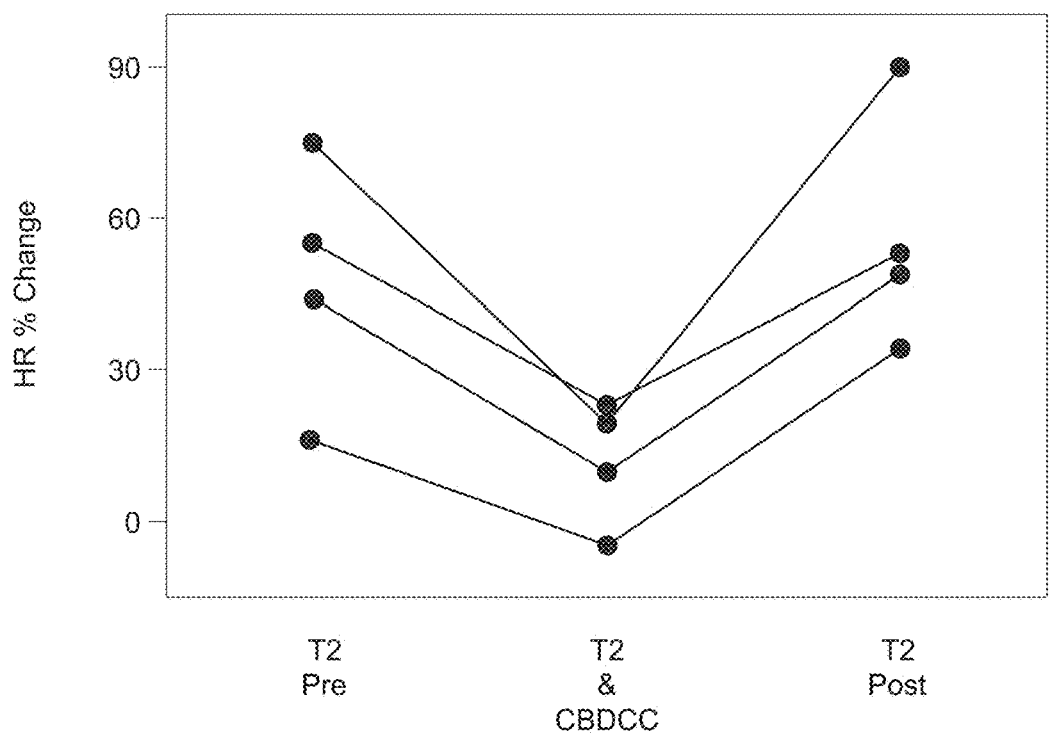
FIGS. 14A-14C show the effects of T2 stimulation on heart rate (FIG. 14A), LV+dp/dt (FIG. 14B) and activation recovery interval of the ventricle (ARI, FIG. 14C) prior to (T2 Pre), during CBDCC, and following CBDCC (T2 Post). *p.0.02 vs T2.
Figure 14B:
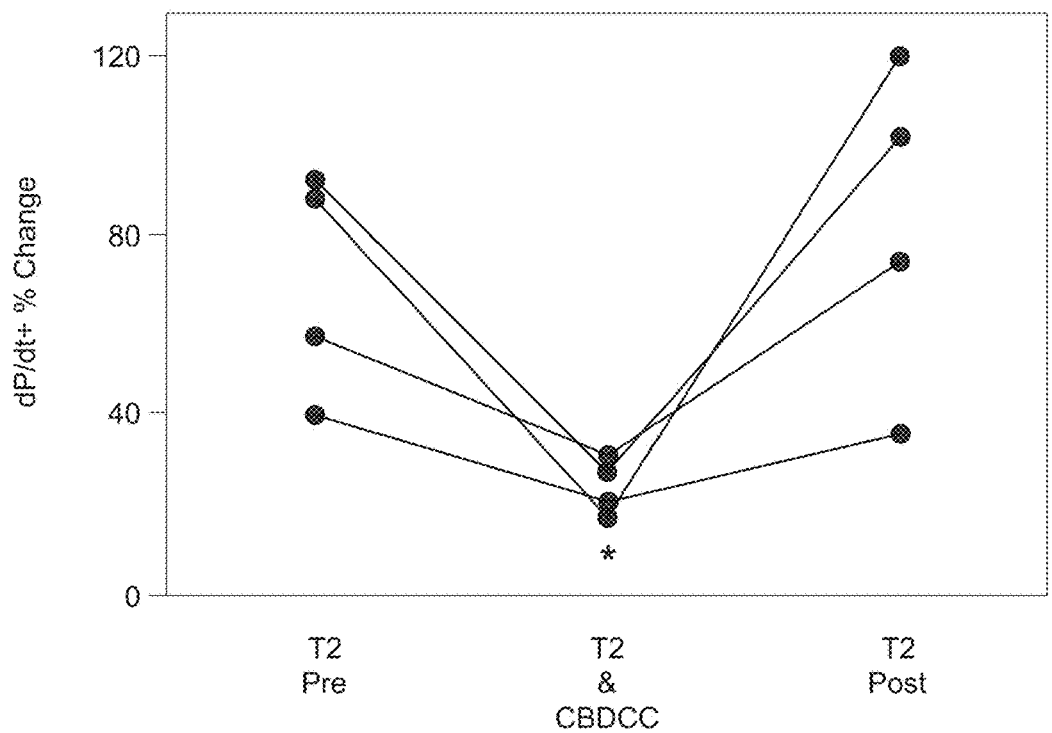
Figure 14C:
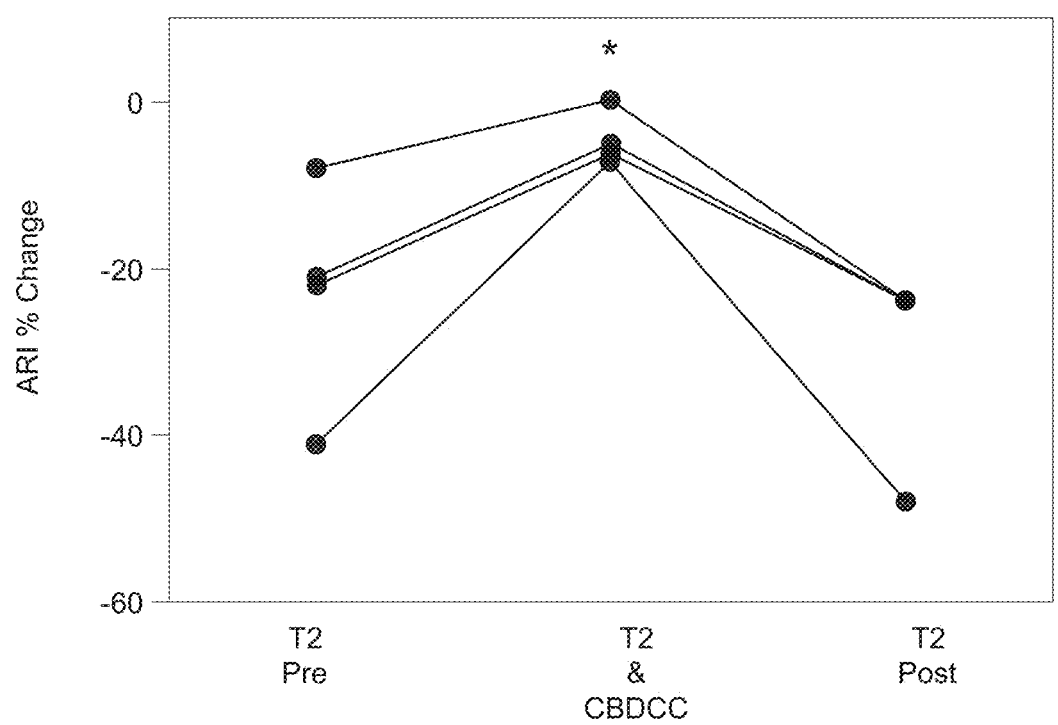

FIG. 14 illustrates the efficacy of CBDCC to reduce sympathetic inputs to the heart as reflected in the blunted responses to T2 stimulation for heart rate (FIG. 14A), LV+dp/dt (FIG. 14B) and ventricular activation recovery interval (ARI, FIG. 14C). As with normal animals, the effects of CBDCC were readily reversible as is evident in the T2 responses evoked post DC block (T2 post, all three panels, FIG. 14A-C).

Figure 15A:
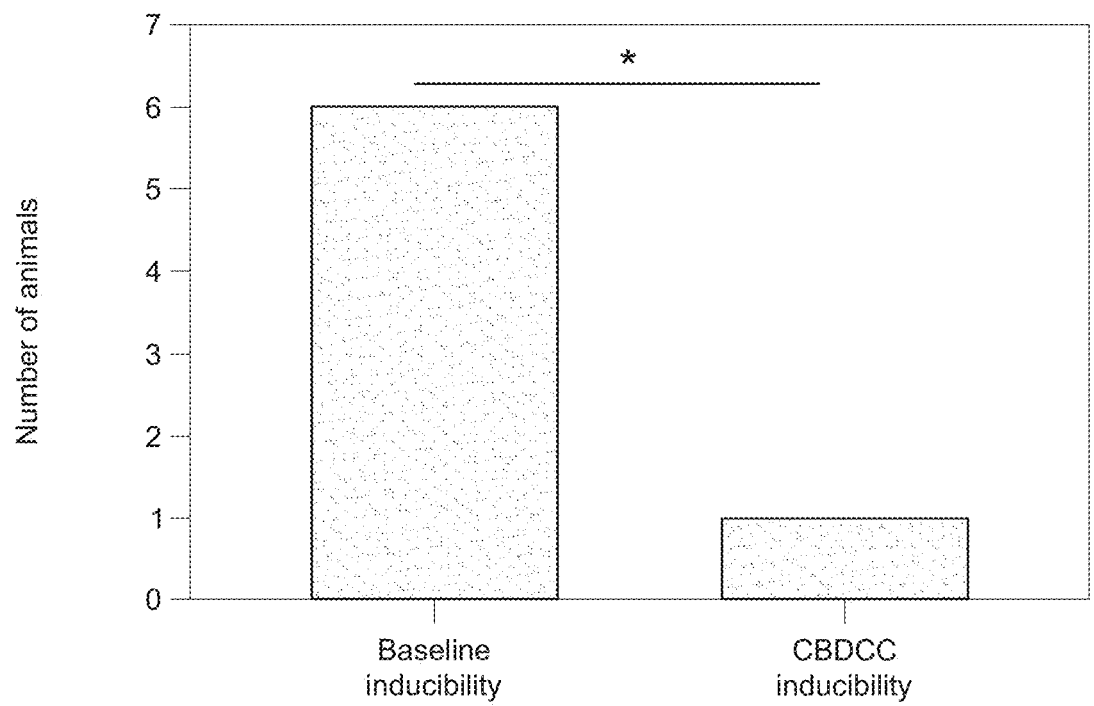
FIG. 15A shows ventricular arrhythmia inducibility of the chronic MI model pigs. Left bar: baseline; right bar: during CBDCC delivery. *P<0.05.

As shown in FIG. 15A, VT was induced at baseline in all animals. Only one animal was re-inducible for VT with simultaneous CBDCC application (p<0.002 from baseline).

Figure 15B:
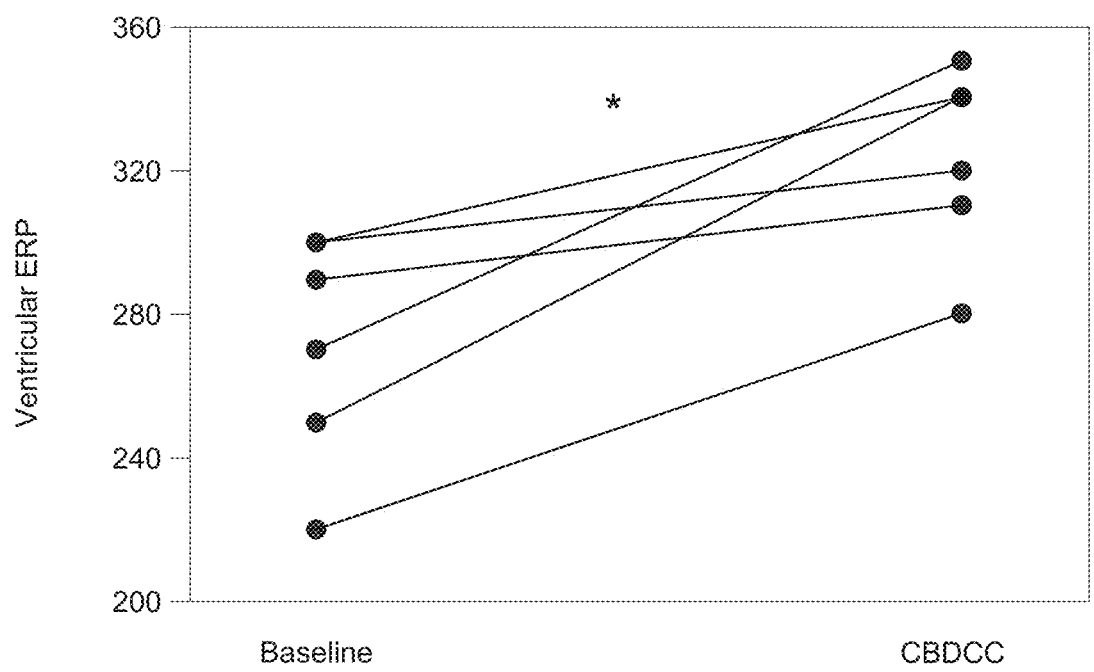

As shown FIG. 15B, S2 effective refractory period (ERP) was prolonged with DCC (323±26 ms) 35 compared to baseline (271±32 ms) (p<0.05).

Table 1 shows that application of the DCC block resulted in reduced contractility and left ventricle end systolic pressure in some pigs but overall did not significantly alter basal cardiac function. This includes ARI which was not altered compared to baseline.

TABLE 1

Cardiac function in in porcine chronic MI model with and without DCC block.

| | Baseline | | | DC | | |
|---|---|---|---|---|---|---|
| | HR | dP/dt+ | LVESP | HR | dP/dt+ | LVESP |
| MI01 | 56 | 1744 | 142 | 67 | 1764 | 137 |
| MI02 | 75 | 1346 | 134 | 72 | 713 | 62 |
| MI04 | 65 | 1419 | 104 | 86 | 1182 | 89 |
| MI05 | 64 | 1350 | 119 | 61 | 819 | 66 |
| MI06 | 64 | 1359 | 106 | 75 | 1383 | 105 |
| M0I7 | 88 | 890 | 80 | 91 | 490 | 86 |

In summary, axonal modulation of the T1-T2 paravertebral chain with CBDCC significantly reduced ventricular arrhythmias in a chronic MI model by 83%. CBDCC altered S2 ERP, without altering baseline ARI, resulting in improved electrical stability.

Conclusion

These studies demonstrated that intervention (e.g. blocking) of the (e.g.) efferent sympathetic nervous system (particularly at the T1-T2 paravertebral ganglia and ansae subclavia) by electrical signals is useful for treating or preventing cardiac dysfunction such as ventricular arrhythmias post-myocardial infarction. The electrical signals reversibly block the efferent system to heart, thereby overriding sympathetic control and affecting ventricular excitability and contractility. This leads to a reduction in arrhythmia potential.

Advantageously, the effects of this approach on other cardiac function is at a minimum. Furthermore, as soon as the electrical signals are removed, the block ceases and the baseline cardiac function in the animal model resumes.

The electrical signals can be delivered in the form of DC or KHFAC. In these studies DC was more effective in producing block with a much lower onset effect. KHFAC, which in contrast produces a high onset effect. Increasing current output was able to produce substantially greater DC block. For sympathetic control, the graded conduction block induced by KHFAC or CBDCC is reversible and scalable. Owing to the KHFAC onset response, CBDCC may be the preferred methodology for arrhythmia management, although there are ways to minimize the onset response.

Finally, in addition to dogs, pig studies revealed that the same efficacy of block was obtained when KHFAC was applied to T1-T2 sympathetic ganglia (when T3 was stimulated). The T1-T2 segment of the paravertebral chain is a principal *nexus* point for modulation of sympathetic projections to the heart.

This suggests that the invention could be put into practice at the very location that surgeons currently perform denervation of T1-T4 sympathetic ganglia.

REFERENCES

[1] Poole et al., NEJM 2008.
Borne et al., JAMA Int Med 2013.
Vaseghi et al., Heart Rhythm, 2014; 11:360-366.
Schwartz, Nat. Rev. Cardiol., 2014; 11, 346-353
Coleman et al., 2012: Circ Arrhythm Electrophysiol; 5(4): 782-8
Hofferberth et al., 2014: J Thorne Cardiovasc Surg; 147(1): 404-9. [7] Bourke et al., Circulation 2010; 121(21):2255-2262.
Aley et al., Neuroscience, 1996; 1083-1090.
Gerges et al. *J. Neural Eng.* 2010 7(6):066003.
Bhadra et al., Annual International Conference of the IEEE Engineering in Medicine and Biology Society. IEEE Engineering in Medicine and Biology Society. Conference 2009: 650-3.
Franke et al. 2014, *J Neural Eng* 11(5):056012.
Lothet et al. 2014, *Neurophotonics* 1(1):011010. Fukuda et al., Cir. Res. 2015; 116(12):2005-2019.
Norris et al., Am. J. Physiol 1974; 227:9-12.
Norris et al., Am. J. Physiol 1977; 233: H655-H659.
Hopkins et al., J Comp Neurol 1984; 229:186-198.
Armour et al., Anatomy of the extrinsic autonomic nerves and ganglia innervating the mammalian heart. In: Randall W C, ed. Nervous control of cardiovascular function. Ner York: Oxford University Press; 1984; 21-67.
[18] Ajijola et al., JACC 2012; 59(1):91-92.
[19] Janes et al., AmJ Cardiol.; 1986; 57:299-309.
[20] White et al., Arch Surg 1933; 26:765-786.
Buckley et al., Hear Rhythm 2016; 13(1): 282-288.
Ajijola et al., Circ Arrhythm Electrophysiol. 2012; 5: 1010-1116.
Han et al., J Am Coll Cardiol. 2012, 59:954-961.
Janes et al., Can. J. Physiol. Pharmacol. 64: 958-969.
Vallbo et al. Physiological Reviews 1979; 59, 919-957.
Macefield et al. The Journal of Physiology (London) 1994; 481, 799-809.
Esler et al. Hypertension, 1988; 11, 3-20.
Brown, G. L. & Gillespie, J. S. Journal of Physiology 1975; 138, 81-102.
Grassi, G. & Esler, M. Journal of Hypertension, 1999; 17, 719-734.
Kilgore et al., Neuromodulation 2014; 17(3): 242-255. us 2011/0160798.
[32] us2011/0125216.
[33] Patel et al. IEEE Transactions on Neural Systems and Rehabilitation Engineering 2017; PP; 99. U.S. Pat. No. 8,843,188 B2.
[35] us2015/0174397.
[36] Franke et al. J Neural Eng 2014; 11(5):056012. WO 2009/058258.
[38] Gwilliam and Horeb, 2008, 168:146-150. U.S. Pat. No. 8,983,614 B2.
[40] us2004/0127953.
[41] U.S. Pat. No. 8,060,208 B2.
[42] WO 02/065896.
Vrabec et al., Med Biol Eng Comput 2016 54:191-203
Journal of Neuroscience Methods 1984; 10:267-75.
Duke et al. J Neural Eng. 2012 June; 9(3):036003.
M. Mirowski, M. D., et. al. N Engl J Med 1980; 303:322-324.
Ackerman et al. Med Biol Eng Comput. 2011; 49:241-251.

The invention claimed is:

1. A device for reversibly inhibiting neural activity of a subject's cardiac-related sympathetic nerve in the extracardiac intrathoracic neural circuit of the subject, the device comprising:
at least one electrode configured to be placed on or around a cardiac-related sympathetic nerve at the ansae subclaviae or at a site along the paravertebral chain between the T1 and T2 ganglia; and
a controller configured to electrically communicate with the at least one electrode, wherein the controller is configured to deliver a therapeutic electrical signal to the at least one electrode,
wherein the therapeutic electrical signal is a kilohertz frequency alternating current (KHFAC) signal or a charge-balanced direct current (DC) signal,
wherein the therapeutic electrical signal is configured to produce a physiological response in the subject, and
wherein the physiological response is a decrease in one or more of at least chronotropic, dromotropic, lusitropic, or inotropic evoked responses.

2. The device of claim 1, wherein the DC signal comprises a cathodic pulse and an anodic pulse.

3. The device of claim 2, wherein the cathodic pulse comprises a current between and including 0.1 mA and 10 mA.

4. The device of claim 1, wherein the KHFAC signal comprises a frequency from 2 kHz to 30 kHz.

5. The device of claim 1, wherein the therapeutic electrical signal is a charge-balanced direct current carousel (CBDCC) signal, or a hybrid of KHFAC and CBDCC.

6. The device of claim 5, wherein the electrical signal comprises a DC ramp and a KHFAC waveform that commences during the DC ramp.

7. The device of claim 5, wherein the therapeutic electrical signal comprises, sequentially:
a DC ramp followed by a plateau and charge-balancing;
a first AC waveform, wherein an amplitude of the first AC waveform increases during a period that the waveform is applied; and
a second AC waveform having a lower frequency and/or lower amplitude than the first waveform.

8. The device of claim 1, wherein the cardiac-related sympathetic nerve is inhibited unilaterally or bilaterally.

9. The device of claim 1, wherein the inhibition is full block or a partial block.

10. The device of claim 1, wherein the at least one electrode is a carousel electrode comprising a plurality of electrode contacts.

11. The device of claim 10, wherein at least one of the plurality of electrode contacts is in signaling contact with the cardiac-related sympathetic nerve.

12. The device of claim 10, wherein the controller is further configured to deliver the therapeutic electrical signal to each of the plurality of electrode contacts in a repeating cycle.

13. The device of claim 10, wherein each of the plurality of electrode contacts is electrically coupled to its own current source or voltage source.

14. The device of claim 13, wherein the controller is further configured to adjust an amplitude of the therapeutic electrical signal delivered to each of the plurality of electrode contacts independently of other electrode contacts.

15. The device of claim 1, wherein the controller is further configured to deliver the therapeutic electrical signal periodically.

16. The device of claim 10, wherein the device comprises at least one sensor configured to detect a physiological parameter related to electrical activity of the heart of a subject, and wherein the sensor is configured to generate a signal indicative of the physiological parameter.

17. The device of claim 16, wherein the electrical activity of the heart of the subject is indicative of cardiac dysfunction or abnormal heart rhythm.

18. The device of claim 16, wherein the controller is further configured to:

receive the physiological signal originating from the sensor;

determine the physiological parameter based at least in part on the physiological signal;

determine whether the physiological parameter meets or exceeds a threshold; and based on the determination that the physiological parameter meets or exceeds the threshold, deliver the therapeutic electrical signal to the at least one electrode.

19. The device of claim 16, wherein the physiological parameter includes one or more of at least heart rate variability, heart rate turbulence, baroreflex sensitivity, heart rate deceleration capacity, or T wave alternans.

20. The device of claim 1, wherein the device is configured for treatment or prevention of one or more of at least heart failure, myocardial infarction, cardiac arrythmias, or ventricular arrhythmias.

* * * * *